United States Patent
Koka et al.

(10) Patent No.: US 12,208,265 B2
(45) Date of Patent: *Jan. 28, 2025

(54) SCALAR TRANSLOCATION DETECTION FOR AN ELECTRODE LEAD OF A COCHLEAR IMPLANT SYSTEM

(71) Applicant: Advanced Bionics AG, Staefa (CH)

(72) Inventors: Kanthaiah Koka, Valencia, CA (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 21 days.

This patent is subject to a terminal disclaimer.

(21) Appl. No.: 18/129,685

(22) Filed: Mar. 31, 2023

(65) Prior Publication Data

US 2023/0233857 A1    Jul. 27, 2023

Related U.S. Application Data

(63) Continuation of application No. 16/640,496, filed as application No. PCT/US2017/048973 on Aug. 28, 2017, now Pat. No. 11,642,525.

(51) Int. Cl.
*A61N 1/36* (2006.01)
*A61N 1/05* (2006.01)

(52) U.S. Cl.
CPC ....... *A61N 1/36039* (2017.08); *A61N 1/0541* (2013.01)

(58) Field of Classification Search
CPC .............. A61N 1/0541; A61N 1/36038; A61N 1/36039

See application file for complete search history.

(56) References Cited

U.S. PATENT DOCUMENTS

| 5,776,179 A | 7/1998 | Ren et al. |
| 11,642,525 B2 * | 5/2023 | Koka ................ A61N 1/36039 607/57 |

(Continued)

FOREIGN PATENT DOCUMENTS

| CN | 106794344 A | 5/2017 |
| WO | 2008048383 | 4/2008 |

(Continued)

OTHER PUBLICATIONS

"International Search Report and Written Opinion received in International Application No. PCT/US2017/048973, dated May 28, 2018."

(Continued)

*Primary Examiner* — Joseph M Dietrich
(74) *Attorney, Agent, or Firm* — ALG Intellectual Property, LLC

(57) ABSTRACT

An illustrative scalar translocation detection system directs a loudspeaker to apply acoustic stimulation to a cochlear implant patient while an electrode lead is inserted into a cochlea of the cochlear implant patient. The system detects a first evoked response to the acoustic stimulation while an electrode is positioned at a first location in the cochlea and detects a second evoked response to the acoustic stimulation while the electrode is positioned at a second location in the cochlea. Then, based on at least one of an amplitude change or a phase change between the first and second evoked responses, the system determines that a scalar translocation of the electrode lead from one scala of the cochlea to another scala of the cochlea has occurred. Based on this determination, the system also notifies a user that the scalar translocation has occurred. Corresponding methods and systems are also disclosed.

20 Claims, 13 Drawing Sheets

(56) References Cited

U.S. PATENT DOCUMENTS

| | | |
|---|---|---|
| 2014/0350640 A1 | 11/2014 | Patrick et al. |
| 2016/0228694 A1 | 8/2016 | Kulkarni et al. |
| 2017/0232257 A1 | 8/2017 | Koka et al. |
| 2017/0239475 A1 | 8/2017 | Koka et al. |

FOREIGN PATENT DOCUMENTS

| | | |
|---|---|---|
| WO | 2010025504 | 3/2010 |
| WO | 2017131675 | 8/2017 |
| WO | 2017182931 | 10/2017 |

OTHER PUBLICATIONS

Holden, et al., "Factors Affecting Open-Set Word Recognition in Adults with Cochlear Implants", Ear Hear. 2013; 34 (3): 342-360.

Kohlloffel, et al.,"Longitudinal Amplitude and Phase Distribution of the Cochlear Microphonic (Guinea Pig) and Spatial Filtering", J. Sound Vib. (1970) 11 (3), 325-334.

O'Connell, et al.,"Electrode Location and Audiologic Performance After Cochlear Implantation: A Comparative Study Between Nucleus CI422 and CI512 Electrode Arrays", Otology & Neurotology 37:1032-1035. 2016, Otology & Neurotology, Inc.

Tasaki, et al.,"The Space-Time Pattern of the Cochlear Microphonics (Guinea Pig), as Recorded by Differential Electrodes", The Journal of the Acoustical Society of America, vol. 24, No. 5, Sep. 1952.

\* cited by examiner

SCALAR TRANSLOCATION DETECTION FOR AN ELECTRODE LEAD OF A COCHLEAR IMPLANT SYSTEM

RELATED APPLICATIONS

This application is a continuation application of U.S. patent application Ser. No. 16/640,496, filed Feb. 20, 2020, which is a U.S. National Stage Application under 35 U.S.C. § 371 of International Application No. PCT/US2017/048973, filed on Aug. 28, 2017, each of which is hereby incorporated by reference in its entirety.

BACKGROUND INFORMATION

Cochlear implant systems are used to provide, restore, and/or improve hearing loss suffered by cochlear implant patients who use the cochlear implant systems. A key component of a cochlear implant system is an electrode lead that is inserted into a cochlea of the patient in a delicate surgical procedure referred to herein as an "insertion procedure." Because insertion procedures are difficult and may result in cochlear trauma or other harm if not done with extreme care, surgeons and other people involved in insertion procedures may desire to carefully monitor and track the electrode lead by identifying its position and insertion path with respect to the cochlea during and after the insertion procedure. It may also be desirable to detect any trauma that may occur to the cochlea as a result of an insertion procedure. For example, trauma may occur when the electrode lead inadvertently translocates from one scala of the cochlea (e.g., the scala tympani) to another scala of the cochlea (e.g., the scala vestibuli) by penetrating through the basilar membrane.

By monitoring the electrode lead and trauma occurring as a result of its insertion, the surgeon or surgical team may be more likely to perform a safe, effective insertion of the electrode lead, thereby resulting in desirable hearing outcomes for patients. Moreover, by determining the final position and insertion path of an electrode lead (e.g., including whether the insertion path includes a scalar translocation), useful data may be determined and studied to improve and facilitate future insertion procedures (e.g., data showing correlation and/or causation between certain hearing outcomes and certain final electrode lead placements, etc.).

Unfortunately, current methods for detecting trauma and identifying the position and/or insertion path of an electrode lead within a patient typically involve imaging technology (e.g., x-ray technology, fluoroscopic technology, CT scanning technology, etc.) that is expensive, inconvenient, and may expose patients to undesirable risk. Moreover, these current methods may be impractical or impossible to employ in real time during insertion procedures, when detecting trauma and identifying the position and/or insertion path of an electrode lead may be of particular value for ensuring proper procedures and securing positive outcomes.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
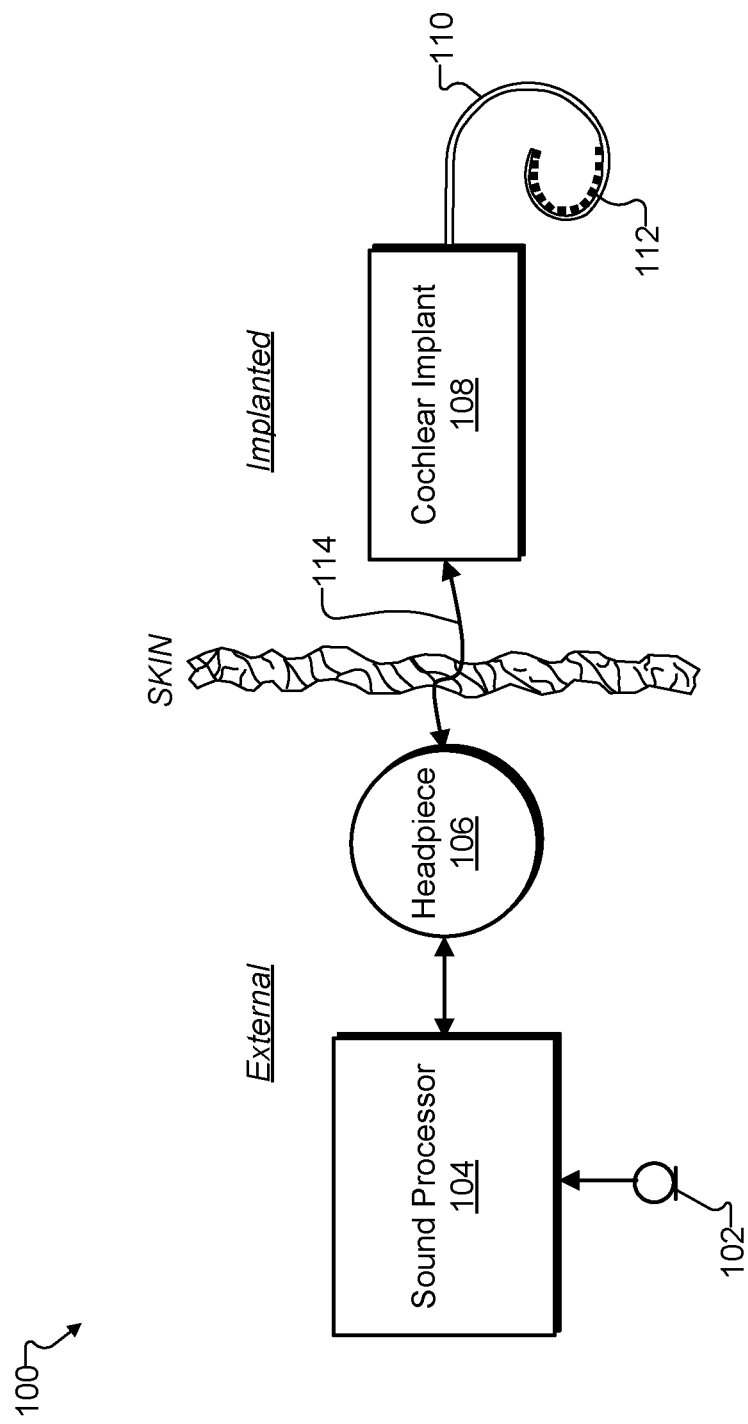
FIG. 1 illustrates an exemplary cochlear implant system according to principles described herein.

Systems and methods for detecting scalar translocation of an electrode lead within a cochlea of a cochlear implant patient are described herein. Detecting a scalar translocation of an electrode lead may assist in detecting trauma and/or identifying the position and/or insertion path of an electrode lead with respect to a cochlea that the electrode lead is inserted into (e.g., in a surgical insertion procedure). As used herein, a "scalar translocation" of an electrode lead refers to a translocation (i.e., a movement from one location to another) of an electrode lead (e.g., a distal end of the electrode lead, in particular) from one scala of the cochlea of a patient (e.g., the scala tympani) to another scala of the cochlea of the patient (e.g., the scala vestibuli). For example, during an insertion procedure whereby an electrode lead is inserted into a cochlea, the electrode lead may travel through the round window into the scala tympani of the cochlea but, instead of continuing to travel through the scala tympani, may inadvertently puncture the basilar membrane and/or other anatomy separating the scala tympani from the scala vestibuli to enter the scala vestibuli. Because such a scalar translocation may damage the basilar membrane (e.g., including hair cells disposed on the basilar membrane and associated with residual hearing of the patient), the translocation of the electrode lead may cause trauma to the cochlea. As such, it may be desirable to detect scalar translocation in real time during the insertion procedure (e.g., so that the scalar translocation may be corrected if possible) and/or after the fact (e.g., so that the scalar translocation may be associated with data being studied to help reduce trauma and improve outcomes in subsequent insertion procedures, or for other suitable purposes as will be described below).

To this end, as will be described in more detail below, an exemplary system for detecting scalar translocation of an electrode lead within a cochlea of a cochlear implant patient may be implemented by at least one physical computing device (e.g., by a computing system coupled to a cochlear implant system, by a sound processor included within a cochlear implant system, by a combination of a computing system and a sound processor included within a cochlear implant system, etc.). The system (e.g., the at least one physical computing device) may detect a first evoked response that occurs in response to acoustic stimulation applied to the cochlear implant patient. For example, the system may detect the first evoked response by way of an electrode configuration including at least one electrode disposed on the electrode lead while the electrode configuration is positioned at a first location along an insertion path of the electrode lead into the cochlea of the patient. The system may further detect a second evoked response that occurs in response to additional acoustic stimulation applied to the cochlear implant patient. For instance, the system may detect the second evoked response by way of the electrode configuration while the electrode configuration is positioned at a second location along the insertion path of the electrode lead into the cochlea (e.g., a second location deeper into the cochlea or nearer to the apex of the cochlea).

Based on the first and second evoked responses, the system may determine at least one of an amplitude change between the first and second evoked responses and a phase change between the first and second evoked responses. Accordingly, based on the amplitude change and/or the phase change, the system may determine whether a scalar translocation of the electrode lead from one scala of the cochlea (e.g., the scala tympani) to another scala of the cochlea (e.g., the scala vestibuli) has occurred.

In certain examples, as mentioned above, disclosed systems and methods may be employed to detect scalar translocation of an electrode lead in real time during an insertion procedure of the electrode lead into a cochlea of a cochlear implant patient. For example, at least one physical computing device included within such a system may, in real time during the insertion procedure, track trauma occurring to the cochlea during the insertion procedure by performing a sequence of scalar translocation determination operations. Specifically, each scalar translocation determination operation may include (e.g., may be implemented by performing) detecting a first evoked response that occurs in response to acoustic stimulation applied to the cochlear implant patient. For instance, the detecting of the first evoked response may be performed by way of an electrode nearest a distal end of the electrode lead at a first time during the insertion procedure while the electrode is positioned at a first location along an insertion path of the electrode lead into the cochlea. Each scalar translocation determination operation may further include detecting a second evoked response that occurs in response to additional acoustic stimulation applied to the cochlear implant patient. As with the detecting of the first evoked response, the detecting of the second evoked response may be performed by way of the same electrode (i.e., the electrode nearest the distal end of the electrode lead) at a second time during the insertion procedure while the electrode is positioned at a second location along the insertion path of the electrode lead into the cochlea.

Each scalar translocation determination operation may further include determining at least one of an amplitude change between the first and second evoked responses and a phase change between the first and second evoked responses, determining (e.g., based on the amplitude change and/or the phase change) whether a scalar translocation of the electrode lead from one scala of the cochlea to another scala of the cochlea has occurred, and determining (e.g., if the determination of whether the scalar translocation of the electrode lead has occurred indicates that the scalar translocation of the electrode lead has occurred) that trauma associated with the scalar translocation has occurred to the cochlea.

Along with performing the sequence of scalar translocation determination operations, the system may further provide a user interface for use by a user associated with the system (e.g., a surgeon or a member of a surgical team performing the insertion procedure), and may provide (e.g., to the user by way of the user interface) information representative of the tracked trauma occurring to the cochlea during the insertion procedure. For instance, the user interface may notify the user when a scalar translocation of the electrode lead has been detected, or may indicate to the user that no scalar translocation of the electrode lead has yet been detected (i.e., that the insertion procedure is so far proceeding without incident).

Disclosed systems and methods for detecting scalar translocation of an electrode lead within a cochlea of a cochlear implant patient may provide various benefits to cochlear implant patients, as well as to surgeons and others involved with insertion procedures. For example, by providing real time information about whether a scalar translocation of the electrode lead or other trauma is occurring during an insertion procedure, disclosed systems and methods may provide a surgeon performing the insertion procedure more information and perspective into the intricate insertion procedure, thereby allowing for a translocated electrode lead to be corrected (e.g., withdrawn and reinserted without scalar translocation) or for trauma to otherwise be mitigated to facilitate a successful outcome of the insertion procedure.

Along with providing perspective into the insertion procedure (e.g., informing surgeons and surgical team members which scala(s) an electrode lead being inserted is currently located in), disclosed systems and methods may further provide data representative of whether a scalar translocation of the electrode lead has occurred, which scala the electrode lead is currently located in, and so forth, to computer systems used to facilitate the insertion procedure. This may allow the computer systems to provide feedback or warnings (e.g., by way of user interfaces, lights, sounds, etc.) that may help the surgeon and other people involved in performing the insertion procedure to proceed with appropriate care at various stages of the procedure. Moreover, in situations where variables such as procedure time, electrode lead location (e.g., current insertion depth), and the like are being tracked along with the cochlear trauma, computer systems may log trauma events to correlate with these other variables to be used in subsequent procedures for other cochlear implant patients (e.g., to warn surgeons to take particular care at particular times or insertion depths, to perform particular actions when an electrode lead is coming up on a depth where a scalar translocation of the electrode lead has previously occurred, etc.).

Even after an insertion procedure is complete, disclosed systems and methods for detecting scalar translocation of electrode leads may be useful for providing insight into a final resting location at which the electrode lead has been inserted. As will be described below, this may be done by detecting evoked responses at two different electrodes located at different locations along the insertion path traveled by the electrode lead at arbitrary times (e.g., at the same time) while the electrode lead is stationary, rather than by the same electrode (e.g., the electrode nearest the distal end of the electrode lead) as the electrode moves from one location at one time to another location at a later time. For example, detecting a scalar translocation of a stationary electrode lead after the insertion procedure may provide useful data for studying effects of scalar translocation and other cochlear trauma on ultimate hearing outcomes such as residual hearing changes over time. Moreover, by using different electrodes (e.g., electrodes X and Y) along the electrode lead to detect evoked responses, an approximate location of a scalar translocation (e.g., a location such as between electrode X and electrode Y on the fully inserted electrode lead) may be determined, providing additional useful data for the patient and for improving insertion procedures to be performed on additional patients in the future.

Additionally, regardless of whether disclosed system and methods for detecting scalar translocation of an electrode lead are performed in real time during an insertion procedure or after the fact when the electrode lead is stationary, the detecting of scalar translocation without use of expensive, inconvenient, or risky imaging technology (e.g., x-ray technology, fluoroscopic technology, CT scanning technology, etc.) may be beneficial. For example, by detecting the scalar translocation of the electrode lead while avoiding these other technologies, patients may be less exposed to various risks, inconveniences, costs, and/or other undesirable aspects associated with such technology.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary cochlear implant system 100. As shown, cochlear implant system 100 may include a microphone 102, a sound processor 104, a headpiece 106 having a coil disposed therein, a cochlear implant 108, and an electrode lead 110. Electrode lead 110 may include an array of electrodes 112 disposed on a distal portion of electrode lead 110 and that are configured to be inserted into the cochlea to stimulate the cochlea after the distal portion of electrode lead 110 is inserted into the cochlea. It will be understood that one or more other electrodes (e.g., including a ground electrode, not explicitly shown) may also be disposed on other parts of electrode lead 110 (e.g., on a proximal portion of electrode lead 110) to, for example, provide a current return path for stimulation current generated by electrodes 112 and to remain external to the cochlea after electrode lead 110 is inserted into the cochlea. As shown, electrode lead 110 may be pre-curved so as to properly fit within the spiral shape of the cochlea. Additional or alternative components may be included within cochlear implant system 100 as may serve a particular implementation.

As shown, cochlear implant system 100 may include various components configured to be located external to a patient including, but not limited to, microphone 102, sound processor 104, and headpiece 106. Cochlear implant system 100 may further include various components configured to be implanted within the patient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a CPI device, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, headpiece 106, and/or any other sound processing unit as may serve a particular implementation).

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil physically coupled to cochlear implant 108). It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the patient via electrodes 112 disposed along electrode lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
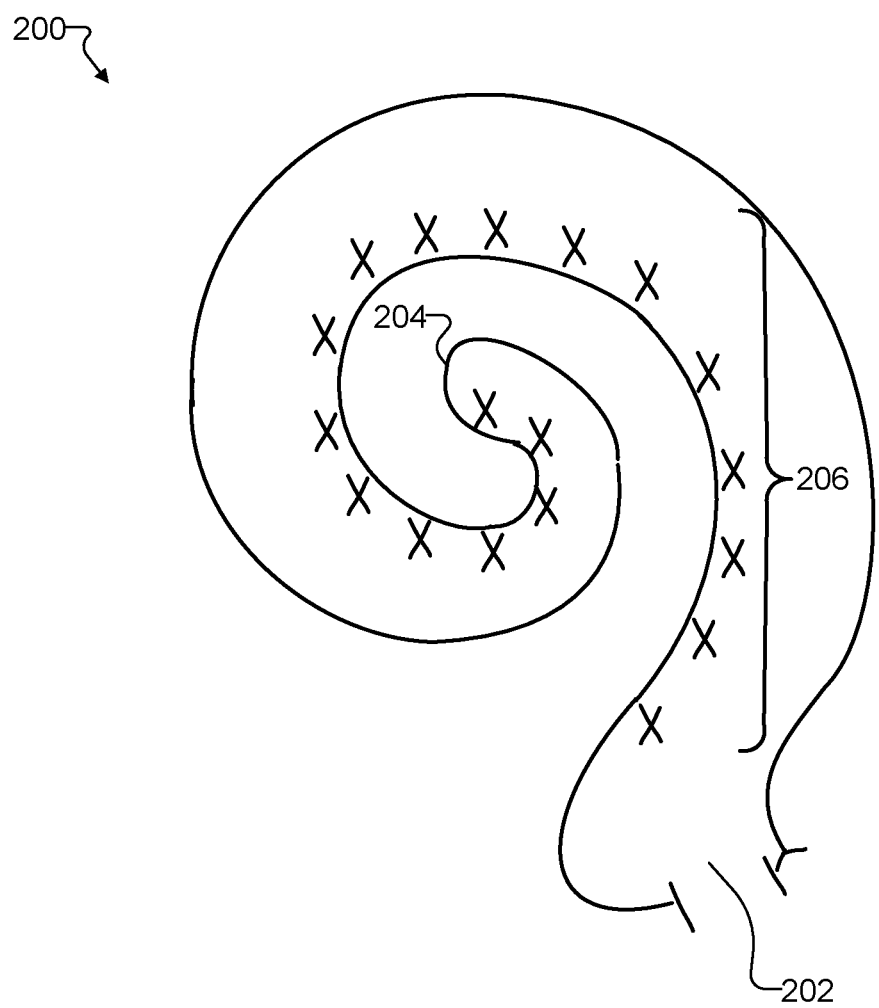
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the electrode lead, the anatomy of the patient's cochlea, and/or any other factor as may serve a particular implementation.

Figure 3:
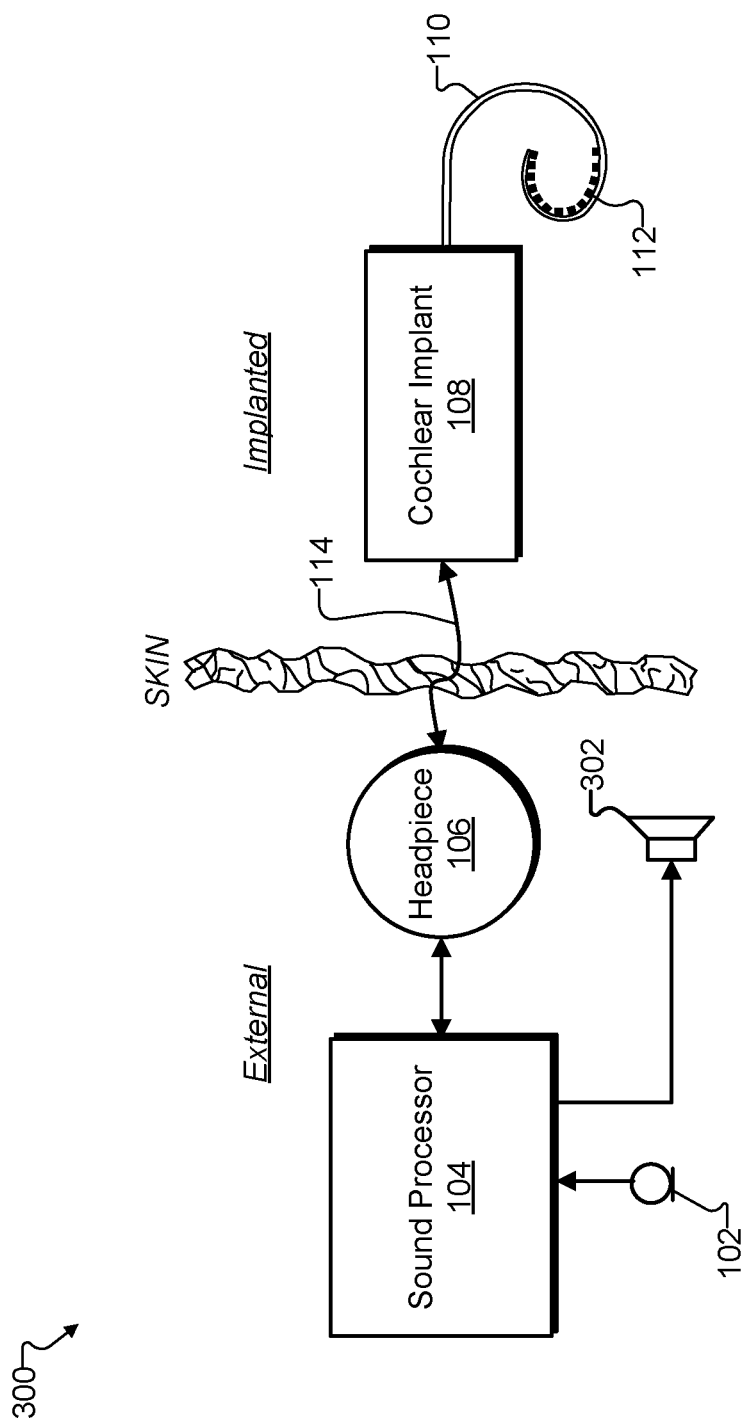
FIG. 3 illustrates an exemplary implementation of the cochlear implant system of FIG. 1 in which the cochlear implant system is implemented as an electro-acoustic stimulation ("EAS") system according to principles described herein.

FIG. 3 illustrates an exemplary implementation of cochlear implant system 100 in which cochlear implant system 100 is implemented as an electro-acoustic stimulation ("EAS") system 300. EAS system 300 may be configured to operate similarly to cochlear implant system 100, except that EAS system 300 may be further configured to provide acoustic stimulation to the patient (e.g., to acoustically stimulate residual hearing that the patient may retain along with electrically stimulating the patient as described above).

As shown, EAS system 300 may include, along with the same components described above with respect to cochlear implant system 100, a loudspeaker 302. Loudspeaker 302 may be in communication with an ear of the patient (e.g., located at an entrance or within the ear canal of the patient). In this configuration, sound processor 104 (which, in EAS system 300, may be referred to as an "EAS sound processor") may be configured to direct loudspeaker 302 to apply acoustic stimulation representative of audio content to one or more stimulation sites within the patient (e.g., within cochlea 200, described above in relation to FIG. 2). For example, loudspeaker 302 may generate the acoustic stimulation used to evoke the evoked responses that may be used to detect the scalar translocation of electrode leads, as described above.

Specifically, for example, a cochlear implant system associated with a particular scalar translocation detection system may be implemented as an EAS system (e.g., EAS system 300) communicatively coupled with the scalar translocation detection system. The EAS system may include a sound processor (e.g., sound processor 104) and a loudspeaker (e.g., loudspeaker 302) communicatively coupled to one another. In accordance with the scalar translocation detection operations described above, the scalar translocation detection system may thus direct the sound processor to direct the loudspeaker to apply the acoustic stimulation for the detection of the first evoked response, and direct the sound processor to direct the loudspeaker to apply the additional acoustic stimulation for the detection of the second evoked response. In some examples, a frequency of the acoustic stimulation and a frequency of the additional acoustic stimulation may be substantially the same. For example, the scalar translocation detection system may direct sound processor 104 to direct loudspeaker 302 to produce a tone at substantially the same frequency for both the acoustic stimulation and the additional acoustic stimulation. Or, as another example, the scalar translocation detection system may direct sound processor 104 to direct loudspeaker 302 to produce a single tone that acts as the acoustic stimulation and the additional acoustic stimulation for evoked responses that are detected simultaneously or closely in time to one another.

In some examples, at least one computing device (e.g., computing devices included within or implementing a scalar translocation detection system, a programming system, etc.) that is separate from (i.e., not included within) cochlear implant system 100 may be communicatively coupled to sound processor 104 for various purposes. For instance, a computing device may be employed to monitor cochlear trauma (e.g., scalar translocation of the electrode lead) during or after an insertion procedure, to otherwise facilitate proper insertion of electrode lead 110 into the cochlea of a patient (e.g., by tracking the insertion depth of the electrode lead or the like), to perform one or more programming or fitting operations with respect to cochlear implant system 100 (e.g., in a clinical setting after the electrode lead has been inserted), and/or for other suitable purposes as may serve a particular implementation. For example, during the insertion procedure, the at least one physical computing device may direct cochlear implant system 100 to perform operations (e.g., generating acoustic stimulation, detecting evoked responses in response to the acoustic stimulation, etc.) for detecting scalar translocation of the electrode lead within the cochlea of the patient. Subsequent to the insertion procedure, the at least one physical computing device may further be used to present audio clips to the patient by way of cochlear implant system 100 in order to facilitate evaluation of how well cochlear implant system 100 is performing for the patient. In other examples, any of these operations may be performed by components of cochlear implant system 100 (e.g., by sound processor 104) without interaction with an external computing device.

Figure 4:
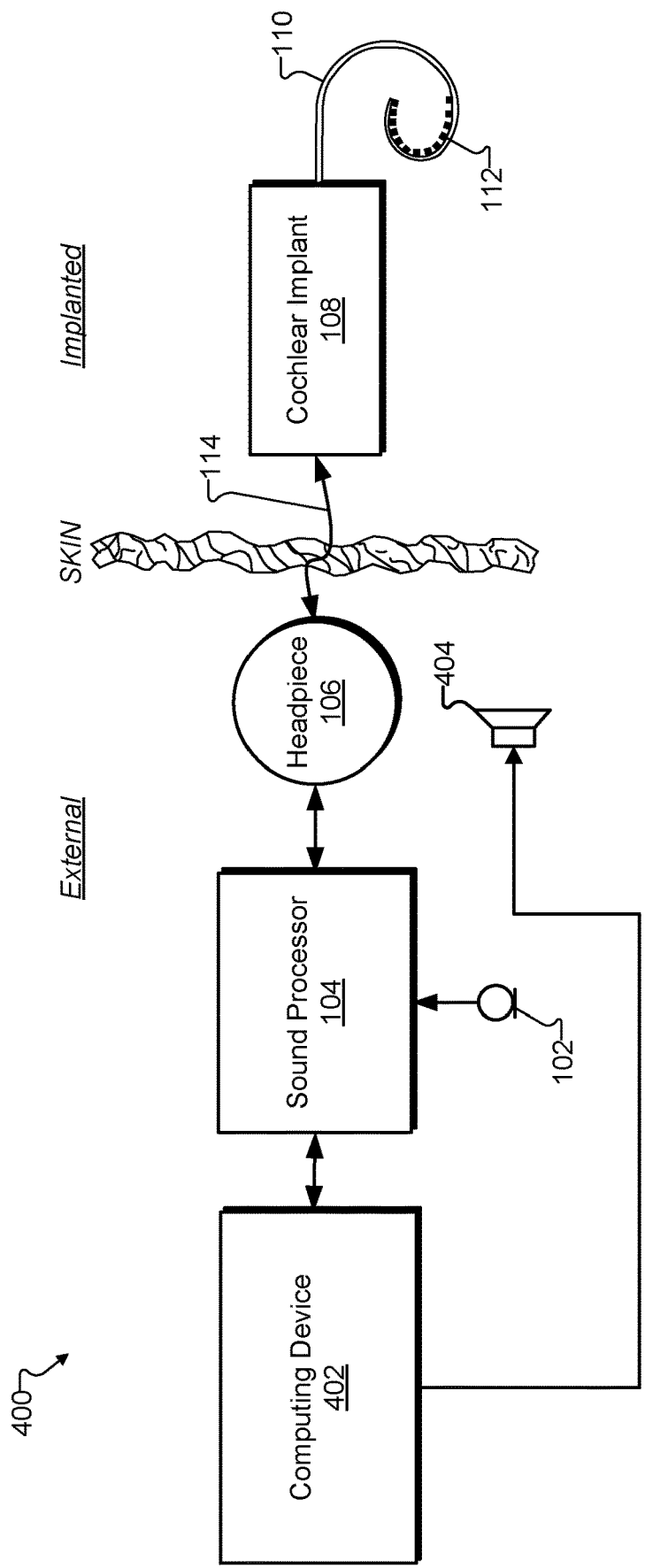
FIG. 4 illustrates an exemplary configuration in which a computing device is communicatively coupled to a sound processor of the cochlear implant system of FIG. 1 according to principles described herein.

To illustrate, FIG. 4 shows an exemplary configuration 400 in which a computing device 402 (e.g., a scalar translocation detection system, programming system, or the like) is communicatively coupled (e.g., by way of a wired or wireless communication channel) to sound processor 104. Computing device 402 may be implemented by any suitable combination of physical computing and communication devices including, but not limited to, a fitting station or device, a programming device, a personal computer, a laptop computer, a handheld device, a mobile device (e.g., a mobile phone), a clinician's programming interface ("CPI") device, and/or any other suitable component as may serve a particular implementation.

In some examples, computing device 402 may provide one or more user interfaces with which a user may interact. For example, a user interface may provide text, graphics, sounds, etc., to facilitate a successful insertion procedure of electrode lead 110 (e.g., by detecting a scalar translocation of the electrode lead) or effective programming of sound processor 104 as may serve a particular implementation. In some implementations, the user interface provided by computing device 402 may include a graphical user interface ("GUI") that allows a user (e.g., a surgeon, a person assisting the surgeon during an insertion procedure, a clinician, etc.) to direct computing device 402 to perform operations for detecting a scalar translocation of the electrode lead within the cochlea. After performing the detection of the scalar translocation (i.e., after determining whether or not a scalar translocation of the electrode lead has occurred), the GUI may provide information representative of the determination by way of visual or audible feedback as may serve a particular implementation (e.g., a beep or red light if a scalar translocation of the electrode lead has occurred, silence or a green light if a scalar translocation of the electrode lead has not occurred, etc.).

As illustrated in FIG. 4, in certain examples, computing device 402 may be communicatively coupled to a loudspeaker 404. As such, computing device 402 may use loudspeaker 404 to generate acoustic stimulation for evoking the evoked responses for non-EAS cochlear implant systems such as cochlear implant system 100 (i.e., systems that, unlike EAS system 300, do not include a dedicated loudspeaker for applying acoustic stimulation to the patient). Specifically, in reference to the scalar translocation detection operations described above, computing device 402 may direct loudspeaker 404 to apply the acoustic stimulation for the detection of the first evoked response, and direct loudspeaker 404 to apply the additional acoustic stimulation for the detection of the second evoked response. Similar to EAS system 300 and loudspeaker 302 described above, in some examples, a frequency of the acoustic stimulation and a frequency of the additional acoustic stimulation may be substantially the same. For example, computing device 402 may direct loudspeaker 404 to produce a tone at substantially the same frequency for both the acoustic stimulation and the additional acoustic stimulation. Or, as another example, computing device 404 may direct loudspeaker 404 to produce a single tone that acts as the acoustic stimulation and the additional acoustic stimulation for evoked responses that are detected simultaneously or closely in time to one another.

While FIG. 4 illustrates computing device 402 communicatively coupled with a cochlear implant system that is not an EAS system (e.g., a cochlear implant system similar to cochlear implant system 100), it will be understood that, in certain examples, computing device 402 or another computing device similarly implementing a scalar translocation detection system may instead be communicatively coupled with an EAS system such as EAS system 300. In such examples, it may not be necessary for computing system 402 to be communicatively coupled to loudspeaker 404 since a loudspeaker included in the EAS system can be used to apply acoustic stimulation to the patient instead (as described above).

Figure 5:
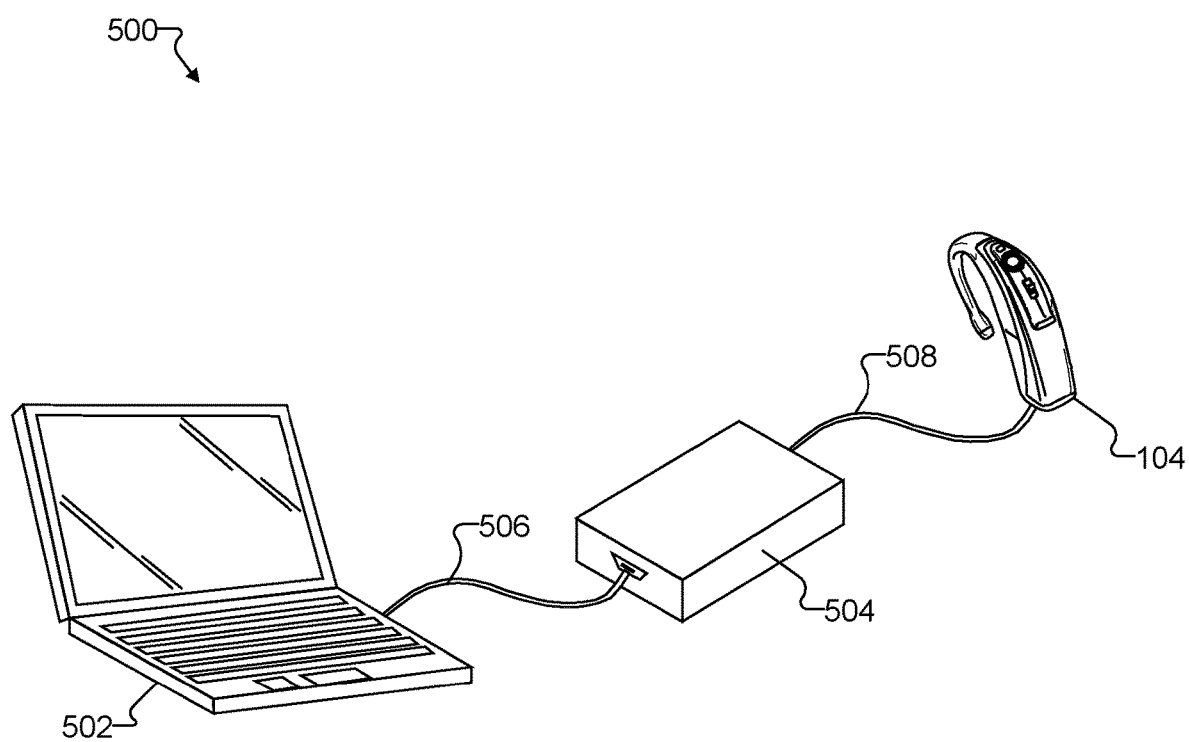
FIG. 5 illustrates an exemplary configuration in which the computing device of FIG. 4 is implemented by a personal computer and a clinician's programming interface device according to principles described herein.

FIG. 5 illustrates an exemplary configuration 500 in which computing device 402 is implemented by a personal computer 502 and a CPI device 504. As shown, personal computer 502 may be selectively and communicatively coupled to CPI device 504 by way of a cable 506. Likewise, CPI device 504 may be selectively and communicatively coupled to sound processor 104 by way of a cable 508. Cables 506 and 508 may each include any suitable type of cable that facilitates transmission of digital data between personal computer 502 and sound processor 104. For example, cable 506 may include a universal serial bus ("USB") cable and cable 508 may include any type of cable configured to connect to a programming port included in sound processor 104.

Figure 6:
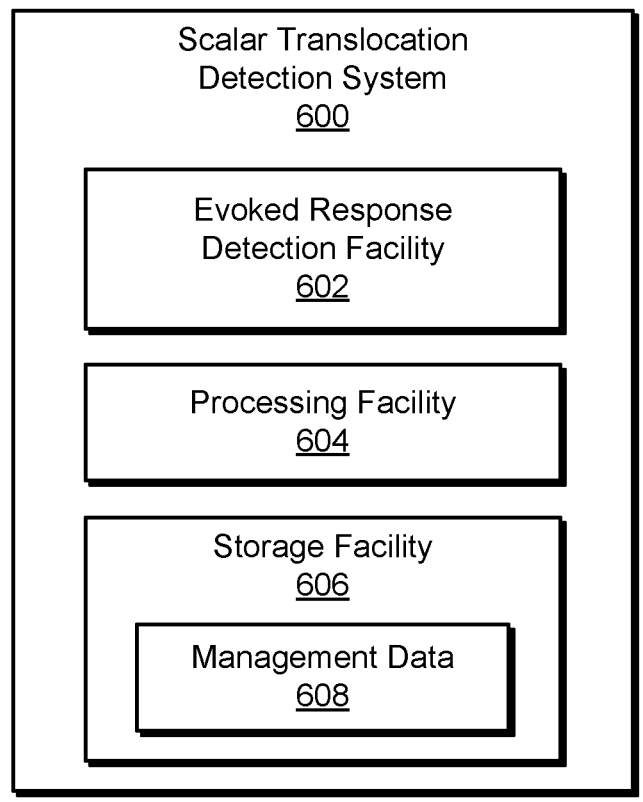
FIG. 6 illustrates a block diagram of exemplary components of a system for detecting scalar translocation of an electrode lead within a cochlea of a cochlear implant patient according to principles described herein.

FIG. 6 illustrates a block diagram of exemplary components of a scalar translocation detection system 600 ("system 600"). System 600 may be configured to perform any of the operations described herein for detecting scalar translocation of an electrode lead within a cochlea of a cochlear implant patient. To this end, as shown, system 600 may include an evoked response detection facility 602, a processing facility 604, and a storage facility 606, which may be selectively and communicatively coupled to one another. It will be recognized that although facilities 602 through 606 are shown to be separate facilities in FIG. 6, facilities 602 through 606 may be combined into fewer facilities, such as into a single facility, or divided into more facilities as may serve a particular implementation. In some examples, system 600 may include, implement, or be implemented by a computing device such as computing device 402, described above. Each of facilities 602 through 606 will now be described in more detail.

Evoked response detection facility 602 may include or be implemented by one or more physical computing devices (e.g., including hardware and/or software such as processors, memories, communication interfaces, instructions stored in memory for execution by the processors, etc.) such as computing device 402, computing components included in sound processor 104, and/or other suitable computing devices that perform various operations associated with detecting evoked responses that occur in response to acoustic stimulation being applied to a cochlear implant patient. For example, evoked response detection facility 602 may generate acoustic stimulation to be applied to the patient or direct a loudspeaker to generate and apply such acoustic stimulation (e.g., directly directing loudspeaker 402 to generate the acoustic stimulation as described in relation to FIG. 4, indirectly directing loudspeaker 302 to generate the acoustic stimulation by way of sound processor 104 as described in relation to FIG. 3, etc.). The acoustic stimulation may be applied to the patient when an electrode configuration (e.g., a single electrode configuration including the electrode nearest the distal end of an electrode lead, a multiple electrode configuration including at least two different electrodes along the electrode lead, etc.) is positioned at a particular location along an insertion path of the electrode lead into a cochlea of the patient.

As such, the acoustic stimulation may cause an evoked response to occur (e.g., to be involuntarily generated by the patient) that may be detected by the electrode configuration at the particular location. The evoked response may be any type of evoked response as may serve a particular implementation. For example, as used herein, an "evoked response" may refer to an electrocochleographic ("ECoG") potential, an auditory nerve response, a brainstem response, a compound action potential, and/or any other type of neural or physiological response that may occur within a patient in response to application of acoustic stimulation to the patient. In some examples, evoked responses may originate from neural tissues, hair cell to neural synapses, inner or outer hair cells, or other sources.

Accordingly, evoked response detection facility 602 may detect, by way of the electrode configuration while the electrode configuration is positioned at a first location along the insertion path of the electrode lead into the cochlea, a first evoked response that occurs in response to the acoustic stimulation applied to the patient. Evoked response detection facility 602 may further detect, by way of the electrode configuration while the electrode configuration is positioned at a second location along the insertion path, a second evoked response that occurs in response to additional acoustic stimulation applied to the patient. For instance, evoked response detection facility 602 may detect the first evoked response by detecting a first ECoG potential occurring in response to the acoustic stimulation, and detect the second evoked response by detecting a second ECoG potential occurring in response to the additional acoustic stimulation. In some examples, the first and second ECoG potentials may be cochlear microphonic potentials. In other examples, other suitable ECoG potentials such as action potentials, summating potentials, or the like may be used in addition to or in place of the cochlear microphonic potentials.

Processing facility 604 may include or be implemented by one or more physical computing devices such as the same computing devices or similar (but separate) computing devices described above in relation to evoked response detection facility 602. Based on evoked responses detected by evoked response detection facility 602 (e.g., the first and second evoked responses described above), processing facility 604 may be configured to determine at least one of an amplitude change between the first and second evoked response and a phase change between the first and second evoked responses. Moreover, based on the determined amplitude change and/or phase change, processing facility 604 may determine whether a scalar translocation of the electrode lead from one scala of the cochlea (e.g., the scala tympani) to another scala of the cochlea (e.g., the scala vestibuli) has occurred. Processing facility 604 may perform these determinations in any suitable way, such as will be described in more detail below.

In some examples, facilities 602 and 604 may perform some or all of the operations described above (e.g., the detections of the first and second evoked responses, the determination of the amplitude change and/or the phase change, the determination of whether the scalar translocation of the electrode lead has occurred, etc.) in real time during an insertion procedure of the electrode lead into the cochlea along the insertion path (e.g., while the surgical insertion procedure is ongoing). As used herein, an operation is considered to be performed in "real time" when the operation is performed immediately and without undue delay (e.g., in real time or near real time). Accordingly, operations may be said to be performed in real time and users of system 600 (e.g., surgeons, surgical team members, etc.) may be considered to receive real time information during the insertion procedure even if the information is provided after a small delay (e.g., up to a few seconds).

In these examples where system 600 is used to perform operations in real time during the insertion procedure, facilities 602 and 604 may be used to continuously and dynamically track trauma as it occurs during the insertion procedure. Specifically, for instance, if the determination by processing facility 604 as to whether the scalar translocation of the electrode lead has occurred indicates that the scalar translocation of the electrode lead has occurred, processing facility 604 may determine that trauma associated with the scalar translocation has occurred to the cochlea. As such, system 600 may track trauma occurring to the cochlea during the insertion procedure by performing a sequence of scalar translocation determination operations each including a respective performance of the detections of the first and second evoked responses (e.g., by evoked response detection facility 602), the determination of the amplitude change and/or the phase change (e.g., by processing facility 604), and the determination of whether the scalar translocation of the electrode lead has occurred (e.g., also by processing facility 604).

As mentioned above, system 600 (e.g., processing facility 604 or another facility not explicitly illustrated in FIG. 6) may facilitate use of the information determined by system 600 by providing a user interface for use by a user associated with system 600 (e.g., using system 600, receiving information from system 600), and by providing information representative of the determination of whether the scalar translocation of the electrode lead has occurred to the user by way of the user interface. This information may be provided in any of the ways described herein, such as by textual, graphical, color-based, audible, or other suitable means.

Storage facility 606 may maintain management data 608 and/or any other data received, generated, managed, maintained, used, and/or transmitted by facilities 602 and 604 in a particular implementation. Management data 608 may include data representative of evoked response measurements that have been made, or data used to make such measurements (e.g., data representative of acoustic stimulation levels, data representative of timing information for detecting voltages in response to generated acoustic stimulation, etc.), or the like. Additionally, management data 608 may include data representative of scalar translocations of electrode leads and/or other trauma that has been detected or data to facilitate such detections. Storage facility 606 may further include any other data as may serve a particular implementation of system 600 to facilitate performing one or more of the operations described herein.

Figure 7:
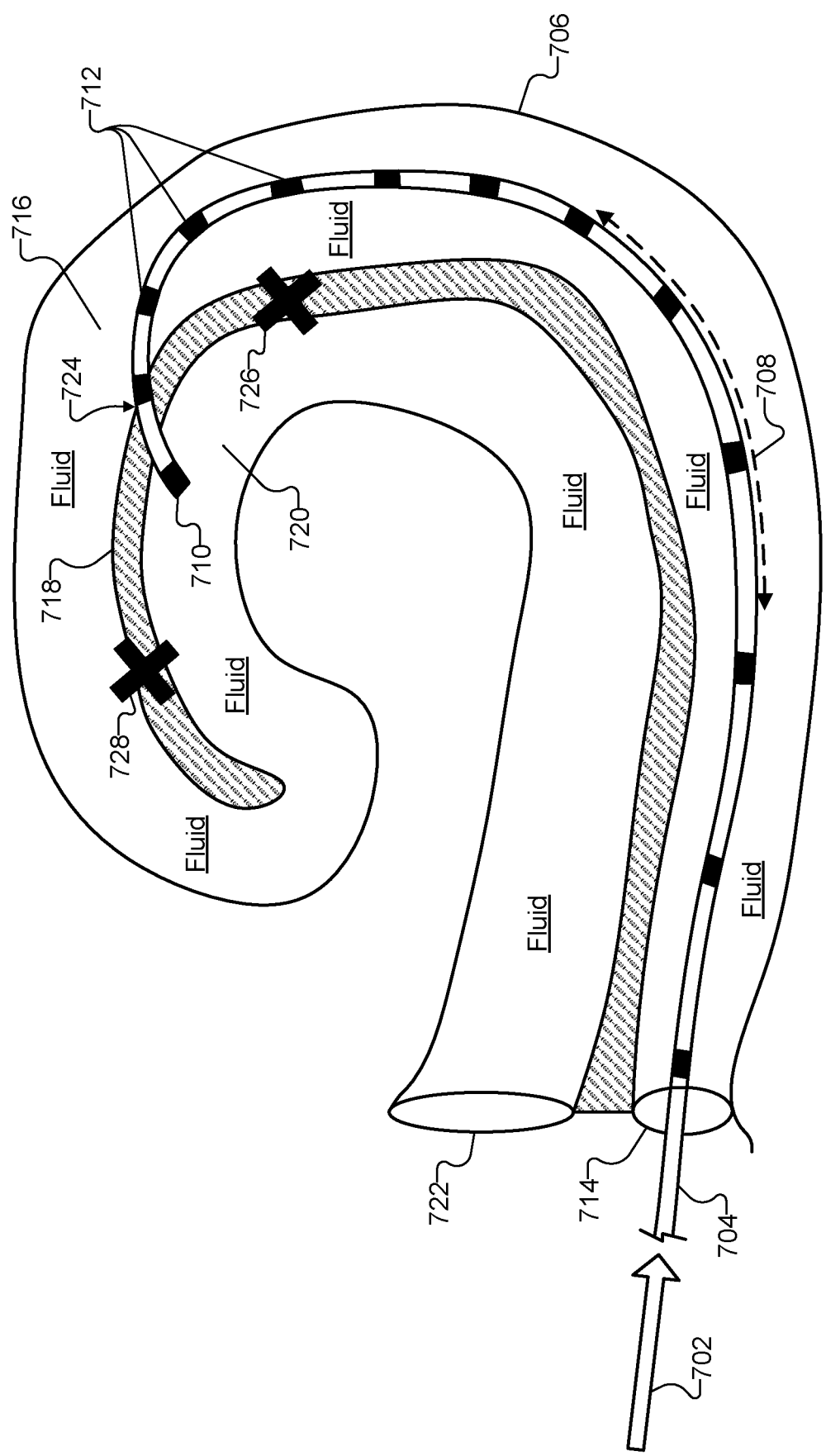
FIG. 7 illustrates exemplary aspects of an electrode lead and of patient anatomy as an exemplary insertion procedure is performed according to principles described herein.

In order to illustrate the context in which an insertion procedure is performed and how a scalar translocation of an electrode lead may occur, FIG. 7 shows exemplary aspects of an electrode lead and of patient anatomy as an exemplary insertion procedure is performed. Specifically, as shown, an insertion procedure 702 is illustrated in which a distal portion of an electrode lead 704 is inserted into a cochlea 706 of a patient along an insertion path 708 (i.e., which is illustrated in part by a dashed curve but will be understood to including the entire path taken by electrode lead 704 within cochlea 706). It will be understood that, while only a distal portion of electrode lead 704 is illustrated in FIG. 7, a proximal portion of the electrode lead not explicitly shown may be coupled to a cochlear implant (also not shown) that may direct current into electrode lead 704, receive and pass on data detected by electrode lead 704 (e.g., evoked response data or the like), and so forth.

As shown, electrode lead 704 may include various electrodes including a leading electrode 710 nearest a distal end of electrode lead 704 and several additional electrodes 712 disposed along the length of electrode lead 704. Unless the context dictates otherwise, it will be understood that electrodes 712, when referred to generally herein, may include all the electrodes disposed on electrode lead 704 including electrode 710 and/or electrodes not explicitly shown in FIG. 7.

As illustrated in FIG. 7, insertion procedure 702 may involve inserting electrode lead 704 through an entry point 714 (e.g., within a round window or cochleostomy of cochlea 706, or another suitable location) and into a scala tympani 716 of cochlea 706. Scala tympani 716 is a chamber of cochlea 706 that is separated by a basilar membrane 718 (e.g., as well as other membranes and anatomical structures not explicitly shown or labeled in FIG. 7) from a scala vestibuli 720 of cochlea 706 (i.e., a separate chamber of the cochlea). As such, vibrations introduced at an oval window 722 of cochlea 706 may vibrate through fluid included in scala vestibuli 720 toward the apex of cochlea 706 and back toward the base of cochlea 706 through fluid included in scala tympani 716. In other words, sound vibrations traveling on either side of basilar membrane 718 may be moving in opposite directions and, as such, may be out of phase with one another. As the vibrations travel through fluid in scala tympani 716, the vibrations may be detected and encoded by hair cells along basilar membrane 718 (if undamaged hair cells are present in the particular patient). Additionally or alternatively, electrodes 712 disposed throughout scala tympani 716 may generate electrical stimulation to stand in for the function of damaged hair cells. Regardless, nerves associated with different depths (i.e., frequency regions) along cochlea 706 may send signals to the brain to effect a hearing sensation, as described above in relation to FIG. 2.

FIG. 7 illustrates electrode lead 704 within cochlea 706 at a particular moment during insertion procedure 702. Specifically, at the moment depicted in FIG. 7, electrode lead 704 has translocated from scala tympani 716, through basilar membrane 718, and into scala vestibuli 720 at a translocation site 724. This scalar translocation of electrode lead 704 may have occurred for any of a variety of reasons during insertion procedure 702, but is most likely an undesirable occurrence because, as shown, the distal end of electrode lead 704 (i.e., at leading electrode 710) has physically penetrated basilar membrane 718, thereby potentially causing trauma to basilar membrane 718 and/or any of various other parts of cochlea 706 associated with basilar membrane 718 (e.g., previously functional hair cells along basilar membrane 718, other membranes or nerves associated with basilar membrane 718, etc.).

To mitigate trauma caused by the scalar translocation of electrode lead 704 and/or to facilitate avoidance of similar scalar translocations in future insertion procedures, a scalar translocation detection system such as system 600 may detect the scalar translocation in any of the ways described herein. For instance, system 600 may detect first and second evoked responses by way of an electrode configuration that includes leading electrode 710 nearest the distal end of electrode lead 704. The detection of the first evoked response may thus be performed by way of electrode 710 at a first time during insertion procedure 702 when electrode 710 is positioned at a first location along insertion path 708 (e.g., a location within scala tympani 716 prior to the moment during the insertion procedure when the scalar translocation of electrode lead 704 occurs). Thereafter, the detection of the second evoked response may be performed by way of electrode 710 at a second time during insertion procedure 702 when electrode 710 is positioned at a second location along insertion path 708 (e.g., the location of electrode 710 within scala vestibuli 720 at the moment depicted in FIG. 7 after the scalar translocation of electrode lead 704 has occurred).

Alternatively, system 600 may, in certain examples, detect first and second evoked responses by way of an electrode configuration that includes a first electrode on electrode lead 704 and a second electrode on electrode lead 704, rather than using the same electrode at two different times as described above. For example, if insertion procedure 702 were to be temporarily suspended or already completed while electrode lead 704 is arranged at the location shown in FIG. 7, system 600 may detect the scalar translocation of electrode lead 704 by way of a multiple-electrode electrode configuration while electrode lead 704 remains stationary. Specifically, system 600 may perform the detection of the first evoked response by way of leading electrode 710 (i.e., which, as shown, is located within scala vestibuli 720) and perform the detection of the second evoked response by way of another electrode 712 included on electrode lead 704 such as the electrode 712 nearest to electrode 710 (i.e., the electrode that, as shown, is located mostly within scala tympani 716 but is nearly breaching basilar membrane 718).

Both evoked responses may be detected simultaneously or at different times as long as electrode lead 704 is disposed, with respect to insertion path 708, such that the distal-most electrode (i.e., electrode 710) is positioned at a first location along insertion path 708 and the other electrode (i.e., the second electrode 712 next to electrode 710) is positioned at a second location along insertion path 708, where the first and second locations are in different chambers of cochlea 706 (e.g., the first location disposed in scala vestibuli 720 and the second location disposed in scala tympani 716). In other words, as used herein, the multiple-electrode electrode configuration that includes both the first and second electrodes may be said to be positioned at both the first location and the second location at the same time if the electrode configuration spans both locations (i.e., at least one electrode included within the multiple-electrode electrode configuration is positioned at each location). Thus, in certain examples, system 600 may detect a first evoked response by way of the multiple-electrode configuration while the electrode configuration is positioned at a first location and detect a second evoked response by way of the multiple-electrode configuration while the electrode configuration is positioned at a second location without the multiple-electrode configuration moving from one location to another (e.g., while the multiple-electrode configuration remains stationary after an insertion procedure is complete).

Regardless of the timeframe over which the first and second evoked responses are detected and/or whether the electrode configurations by way of which the evoked responses are detected use single or multiple electrodes, system 600 may determine an at least one of an amplitude change between the first and second evoked responses and a phase change between the first and second evoked responses. Based on the amplitude change and/or the phase change that has been determined, system 600 may determine that the scalar translocation of electrode lead 704 from scala tympani 716 to scala vestibuli 720 has occurred. System 600 may provide this information to a user to be used in any of the ways described herein. For example, the information may be used to inform a surgical team that electrode lead 704 should be backed out and reinserted to try to avoid the scalar translocation prior to completing insertion procedure 702, the information may be stored for reference in later insertion procedures (e.g., to inform surgical teams to take extra care at particular times or depths during the later insertion procedures), the information may be used by researchers studying the effects of scalar translocations of electrode leads to inform the researchers that a scalar translocation has occurred with respect to cochlea 706, and so forth as may serve a particular implementation.

In certain examples, the approximate depth of electrode lead 704 into cochlea 706 may be known or determined at a particular time. As such, because the scalar translocation of electrode lead 704 may be determined to have occurred between, for instance, electrode 710 and the electrode 712 adjacent to electrode 710, system 600 may further determine approximately where scalar translocation site 724 is located within cochlea 706 (e.g., in terms of a cochlear depth, a frequency range, etc.).

As described above, system 600 may determine whether a scalar translocation of an electrode lead such as electrode lead 704 has occurred based on a determined amplitude change and/or phase change detected between a first evoked response detected at a first location and a second evoked response detected at a second location. This is because an evoked response may be expected to have a significantly different amplitude and phase if detected at a location within scala vestibuli 720 as compared to if the evoked response is detected at a location within scala tympani 716. Specifically, as will be described and illustrated in more detail below, an evoked response detected by the electrode configuration at a translocated location within cochlea 706 (e.g., a location within scala vestibuli 720 in the example of FIG. 7) may have a significantly lower amplitude and a phase approximately 180° offset from an evoked response detected by the electrode configuration at a non-translocated location within cochlea 706 (e.g., a location within scala tympani 716, where electrode lead 704 is aimed to be kept during insertion procedure 702).

As such, in certain examples, system 600 may determine whether the scalar translocation of the electrode lead has occurred based on a notable drop off in amplitude and/or phase from one evoked response measurement to another. However, in other examples, this determination may be complicated by the fact that other factors may also cause amplitude and/or phase changes to be detected between different cochlear locations along the insertion path, even if no scalar translocation of the electrode lead has occurred. Specifically, for example, evoked responses at locations within the cochlea leading up to a depth associated with a particular frequency (e.g., a frequency at which acoustic stimulation is applied to evoke the evoked responses being detected) may be detected to have increasing amplitudes, while evoked responses at locations within the cochlea leading away from the location associated with the particular frequency may be detected to have decreasing amplitudes.

To illustrate, FIG. 7 shows an exemplary depth 726 that may be associated with (i.e., may correspond to within the tonotopically arranged structure of the cochlea described above in relation to FIG. 2) an exemplary frequency at which acoustic stimulation may be applied to the patient (e.g., to evoke the evoked responses being detected). Additionally, FIG. 7 shows an exemplary depth 728 beyond depth 726 (i.e., nearer to the apex of cochlea 706) that may represent an anticipated final insertion depth of electrode lead 704 after insertion procedure 702 is complete. As the one or more electrodes included in the electrode configuration being used to detect evoked responses pass through entry point 714 and approach depth 726, the amplitudes of evoked responses detected may be expected to grow increasingly larger. However, once the electrode configuration detecting the evoked responses passes depth 726 to continue on toward depth 728, amplitudes of evoked responses detected may be expected to get increasingly smaller (e.g., dropping off by 1/e uV/mm in certain examples, where e represents Euler's number, which is approximately equal to 2.718). As such, a threshold used by system 600 to analyze whether a detected amplitude change may be indicative of a scalar translocation of the electrode lead may be dependent on both a frequency at which acoustic stimulation is applied to the patient to evoke the responses (e.g., the frequency associated with depth 726) as well as the ultimate depth (e.g., depth 728) and/or a current depth at which the evoked responses are being detected, insofar as the current depth may be determined. For example, if depth 728 is nearer to the apex of cochlea 706 than depth 726 as shown in FIG. 7, then a detected drop off in evoked response amplitudes detected by way of electrode 710 may indicate either that electrode 710 has passed depth 726 or that electrode 710 has translocated into scala vestibuli 720. As such, the threshold against which amplitude measurements are compared may take this into account (e.g., allowing for an amplitude drop less than a particular threshold such as about 1/e uV/mm in some examples before determining that a scalar translocation of the electrode lead may have occurred).

Figure 8A:
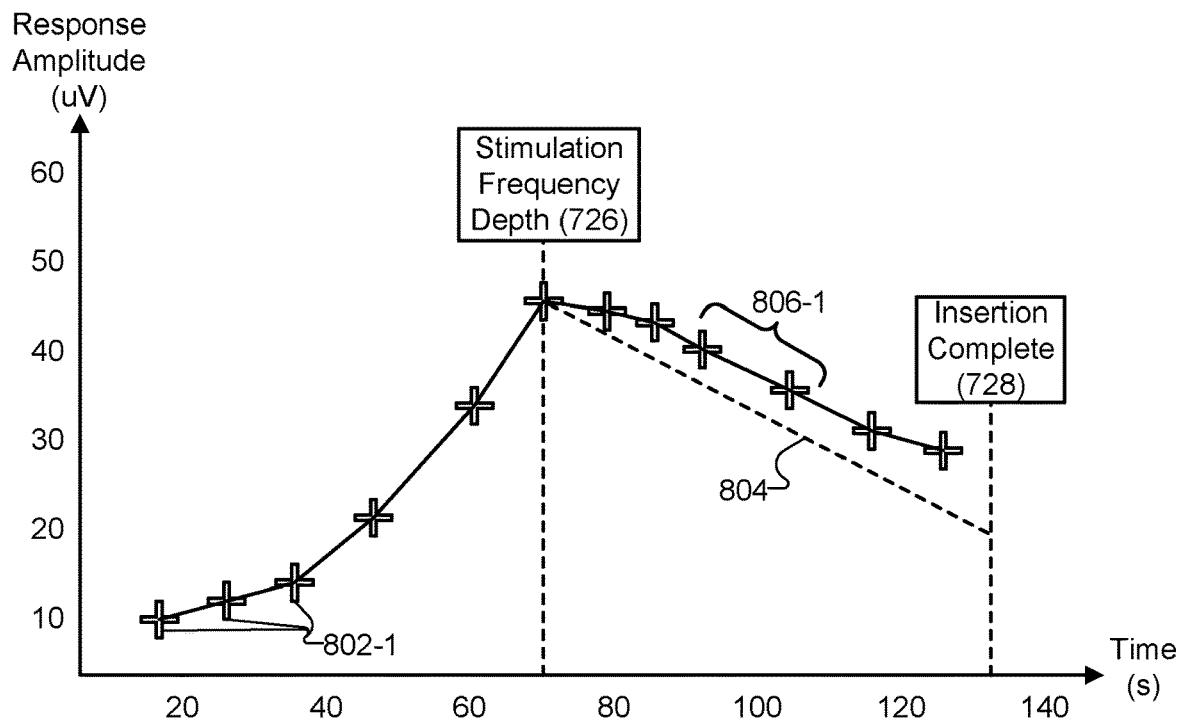
FIGS. 8A-8B illustrate graphs of amplitude measurements of exemplary evoked responses detected during exemplary insertion procedures according to principles described herein.
Figure 8B:
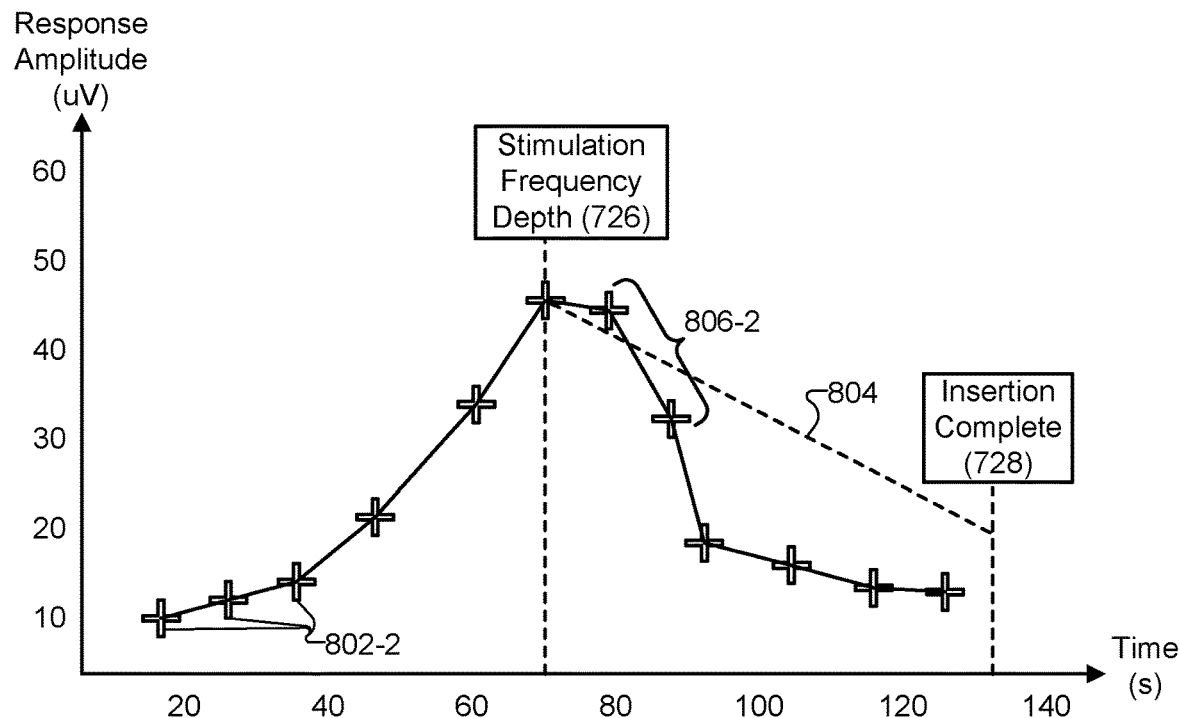

To illustrate, FIGS. 8A-8B show graphs 800 (i.e., graphs 800-1 in FIG. 8A and 800-2 in FIG. 8B) of amplitude measurements 802 (e.g., amplitude measurements 802-1 in graph 800-1 and amplitude measurements 802-2 in graph 800-2) of exemplary evoked responses detected during exemplary insertion procedures. For example, graph 800-1 in FIG. 8A may illustrate an exemplary insertion procedure in which no scalar translocation of the electrode lead occurs, while graph 800-2 in FIG. 8B may illustrate a different exemplary insertion procedure (e.g., such as insertion procedure 702) in which a scalar translocation of the electrode lead does occur.

Both graphs 800, as well as additional graphs that will be described in more detail below, illustrate measurements taken over a period of time indicated by the x-axis. For example, these graphs may represent measurements made by way of a single electrode (e.g., a leading electrode such as electrode 710) during an insertion procedure. During an insertion procedure, measurements of evoked responses (e.g., amplitude measurements, phase measurements, etc.) may be made automatically at a constant rate (e.g., once every 100-200 ms or at another suitable rate). As such, time may be closely tied to and/or may serve as a useful analog for insertion depth or electrode position within the cochlea because the electrode lead is being inserted deeper into the cochlea as time passes during the procedure.

In some insertion procedure examples, systems may be in place to detect real time insertion depth of a lead as the lead is being inserted into the cochlea, and to correlate that insertion depth with amplitude or other measurements of evoked responses. Hence, in such examples, amplitude graphs such as graphs 800 (e.g., and/or phase graphs such as will be described below) may be provided (e.g., to surgeons and/or others performing the insertion procedure) that represent measured amplitude and/or phase values with respect to insertion depth or electrode position within the cochlea, rather than (or in addition to) with respect to time. Similarly, it will be understood that principles described and illustrated herein with respect to time may apply with respect to measurements taken on a stationary electrode lead by way of different electrodes. Here again, the time at which such measurements are made may be less significant than the respective cochlear depths of the different electrodes performing the measurements. Hence, in these examples as well, graphs such as those illustrated in FIGS. 8A and 8B, as well as other graphs illustrated below, may be drawn with respect to cochlear depth, electrode position within the cochlea, or something else other than time.

As shown in FIG. 8A, consecutive measurements 802-1 increase until the electrode configuration by way of which each measurement 802-1 is being made reaches a stimulation frequency depth (i.e., a depth within the cochlea associated with a frequency at which acoustic stimulation is being applied to the patient). For instance, depth 726 illustrated in FIG. 7 and described above may represent one example of such a stimulation frequency depth. After continuing past the stimulation frequency depth, graph 800-1 shows that amplitude measurements 802-1 begin to drop off. However, because the drop off occurs at a rate less than a predetermined amplitude threshold 804 (i.e., causing measurements 802-1 to stay above or approximately with a rate represented by amplitude threshold 804), system 600 may recognize that this amplitude drop off does not indicate a scalar translocation of the electrode lead, but instead indicates that the stimulation frequency depth has been passed by the measuring electrode.

In scenarios where amplitude measurements 802-1 are being made during an insertion procedure (e.g., rather than with a stationary electrode lead after the insertion procedure) and where real-time lead insertion depth information is not available to correlate to measurements (e.g., but where time information is available), it will be understood that predetermined amplitude threshold 804 may be dependent on an average insertion speed for the particular insertion procedure. For example, predetermined amplitude threshold 804 may be a larger threshold (i.e., a steeper line) if a particular insertion procedure is progressing more rapidly than if the insertion procedure is progressing relatively slowly. Additionally, if measurements are made at a constant rate, it will be understood that changes between measurements (e.g., amplitude measurements 802-1, as well as phase measurements described below) may be most useful (i.e., may yield the most accurate information) when the insertion speed of the lead into the cochlea remains relatively constant. Conversely, in scenarios where measurements are made while the electrode lead is stationary (e.g., and the measurements are thus represented with respect to insertion depth of the different electrodes rather than with respect to time), considerations such as insertion speed may not be relevant.

As shown, system 600 may determine whether the scalar translocation of the electrode lead has occurred by determining that an amplitude change 806-1 (also referred to as an amplitude drop 806-1) between first and second evoked responses is less than amplitude threshold 804. For example, amplitude change 806-1 may be the difference between amplitude measurements 802-1 associated with two consecutive evoked responses that are measured by system 600 and amplitude threshold 804 may be associated with the stimulation frequency depth at which acoustic stimulation is being applied in order to evoke the responses represented by amplitude measurements 802-1, and may be expressed as an amplitude rate of change with respect to time (e.g., based on a constant time between each measurement and an average insertion speed of a lead) or with respect to insertion depth (e.g., a constant rate such as 1/e uV/mm). System 600 may then determine (e.g., in response to the determination that amplitude change 806-1 is less than amplitude threshold 804) that the scalar translocation of the electrode lead has not occurred. In other words, system 600 may determine that, while the amplitude measurements 802-1 associated with amplitude change 806-1 do drop off significantly, the amplitude drop may be explained by passing the stimulation frequency depth and therefore is not considered to be indicative of a scalar translocation of the electrode lead.

Similarly, as shown in the example of graph 800-2 of FIG. 8B, consecutive measurements 802-2 increase until the electrode configuration reaches the stimulation frequency depth, and then, after continuing past the stimulation frequency depth, begin to drop off. However, in graph 800-2, the rates of decrease between certain amplitude measurements 802-2 are much greater than the rates of decrease shown in graph 800-1. For example, an amplitude change 806-2 (also referred to as an amplitude drop 806-2) between first and second evoked responses represented by amplitude measurements 802-2 associated with amplitude change 806-2 shows a drop off considerably more significant than the amplitude threshold 804 (i.e., causing measurements 802-2 to drop below the rate represented by amplitude threshold 804). Accordingly, system 600 may determine that this amplitude drop may indeed indicate that a scalar translocation of the electrode lead has occurred and may proceed to verify whether such a scalar translocation has occurred by analyzing a corresponding phase change associated with amplitude drop 806-2.

It will be understood that in certain examples, the magnitude of amplitude drop 806-2 may, in and of itself, indicate that the scalar translocation of the electrode lead has occurred and system 600 may determine as much from amplitude measurements 802-2 alone. However, in other examples, it may be necessary or desirable to verify that the scalar translocation of the electrode lead has occurred by analyzing a corresponding phase change as will be described below. By the same token, it will be understood that, because the phase change of evoked responses may further indicate, along with the amplitude change, whether a scalar translocation is likely to have occurred, amplitude threshold 804 may be set so as to not take into account an amplitude drop expected after the electrode configuration passes the stimulation frequency depth. For example, amplitude threshold 804 may be set (i.e., predetermined at a level) such that both amplitude drops 806-1 and 806-2 would be greater than amplitude threshold 804 and would indicate the possibility of a scalar translocation of the electrode lead. Thus, in this example, an analysis of a phase change associated with each amplitude drop 806 could be used to determine whether the scalar translocation of the electrode lead has occurred or whether the stimulation frequency depth has merely been passed by the electrode configuration measuring the evoked responses.

Figure 9:
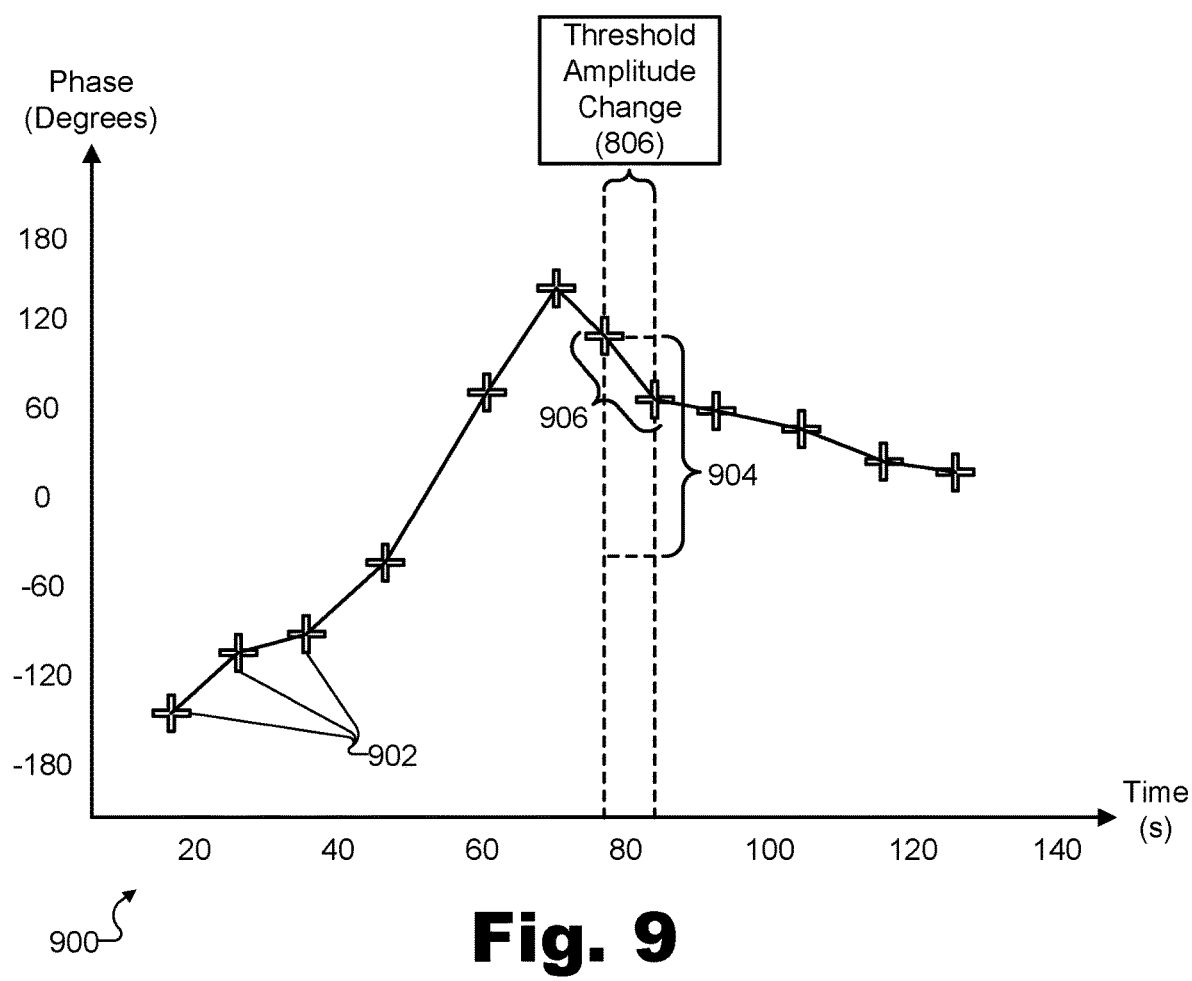
FIGS. 9-11 illustrate graphs of phase measurements of exemplary evoked responses detected during exemplary insertion procedures according to principles described herein.
Figure 10:
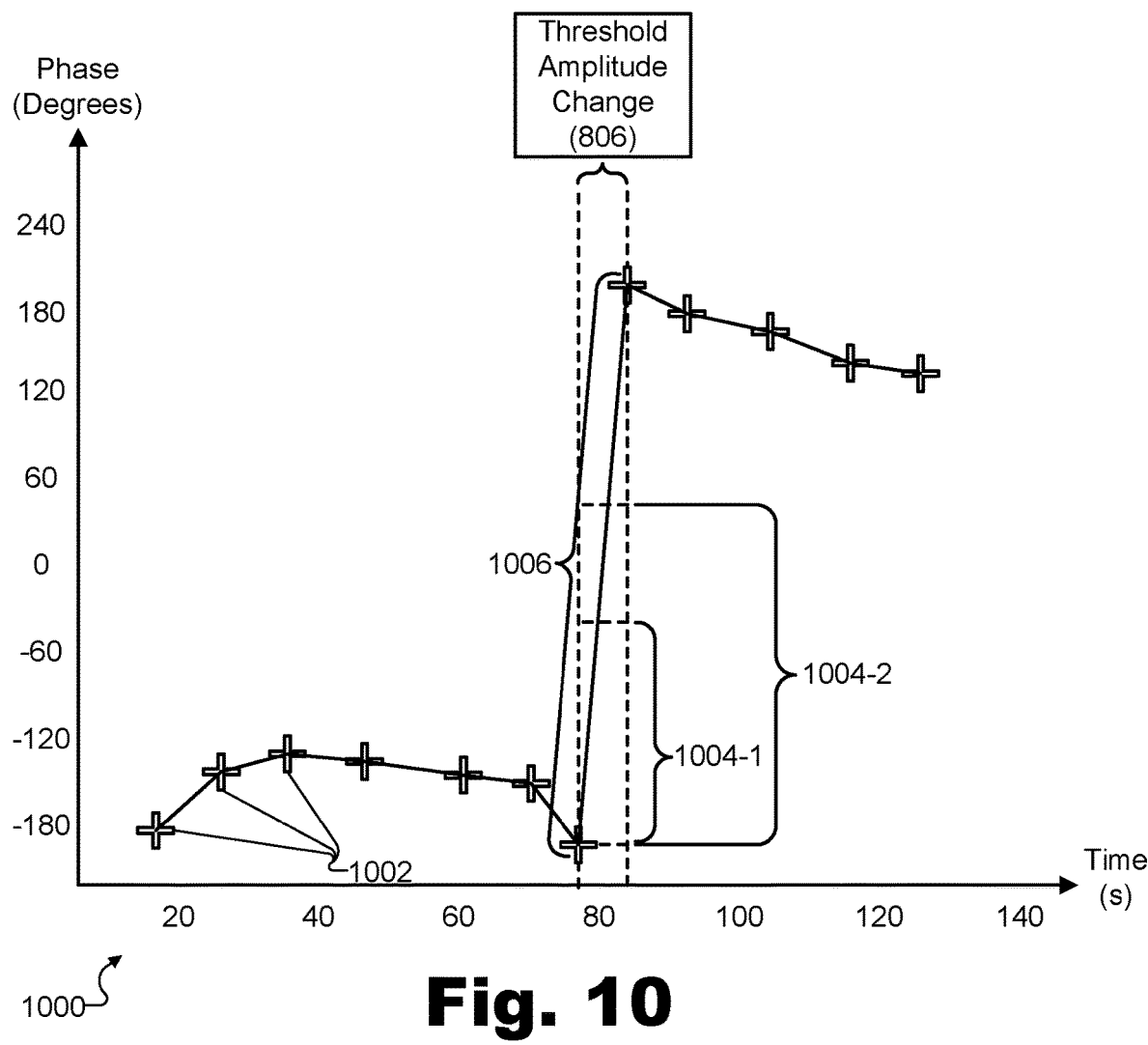
Figure 11:
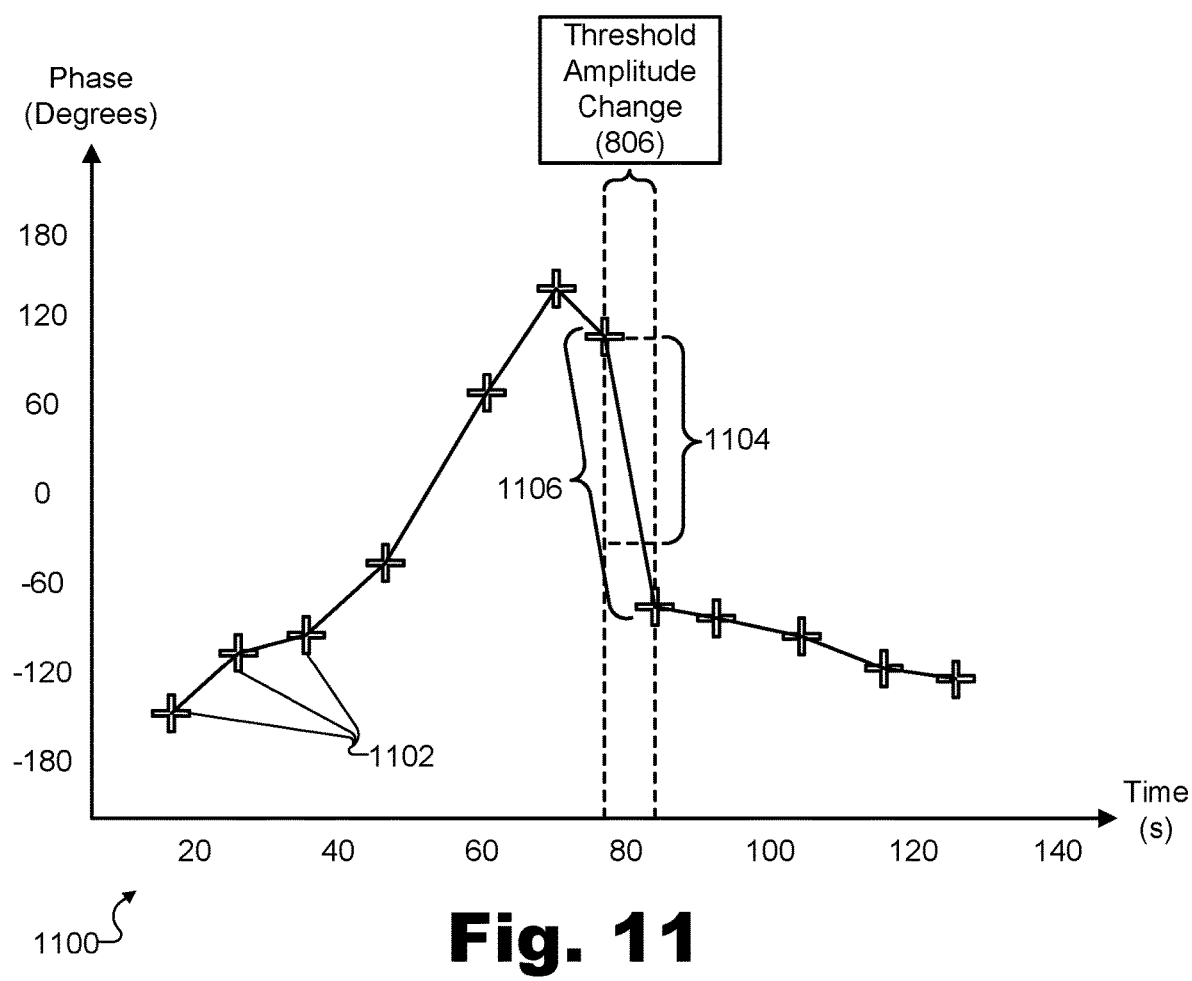

To illustrate how a phase change corresponding to a threshold amplitude change may be used to determine whether (or verify that) a scalar translocation of the electrode lead has occurred, FIGS. 9 through 11 show respective graphs of phase measurements of exemplary evoked responses detected during exemplary insertion procedures with respect to time. The threshold amplitude change illustrated in each of FIGS. 9 through 11 may represent an amplitude drop greater than a predetermined amplitude threshold such as illustrated by amplitude drop 806-2 (or by an amplitude drop like 806-1 in examples where, as mentioned above, amplitude threshold 804 is set so as to not take into account an expected amplitude drop after the stimulation frequency depth is passed by the electrode configuration measuring the evoked responses). As such, FIGS. 9 through 11 illustrate respective phase changes corresponding to such threshold amplitude changes. In other words, phase changes that may be analyzed by system 600 (i.e., due to a corresponding threshold amplitude change) are marked with boxes labeled "Threshold Amplitude Change (806)" in FIGS. 9 through 11.

As mentioned above, if a scalar translocation of the electrode lead occurs, a phase change of approximately 180° (i.e., π radians) is expected to be detected between evoked responses associated with a location in one scala of the cochlea (e.g., the scala vestibuli) and evoked responses associated with a location in another scala of the cochlea (e.g., the scala tympani). However, detecting smaller phase changes between different locations within the same scala of the cochlea is also normally to be expected. Accordingly, system 600 may determine that the scalar translocation of the electrode lead has occurred only if a phase change (e.g., between two consecutive evoked response measurements) is detected to be approximately 180° for evoked responses that correspond to an amplitude drop that exceeds an amplitude threshold such as amplitude threshold 804. For instance, system 600 may detect that the phase change is greater than one phase threshold (e.g., a phase threshold less than 180°) and, in some examples, that the phase change is also less than another phase threshold (e.g., a phase threshold greater than 180°).

For example, a graph 900 shown in FIG. 9 illustrates a plurality of phase measurements 902 plotted along graph 900. As described above in relation to FIGS. 8A and 8B, while phase measurements 902 in graph 900 are plotted with respect to time (e.g., the time elapsing during an insertion procedure such as insertion procedure 702) in FIG. 9, it will be understood that, in other examples, phase measurements 902 may be plotted with respect to insertion depth. While not explicitly stated, it will be further understood that this may also be the case for other graphs depicting phase measurements described below in FIGS. 10 and 11.

As shown, a predetermined phase threshold 904 (e.g., a threshold large enough to allow for minor phase changes but small enough to be surpassed by a phase change of approximately 180°) is depicted relative to a first phase measurement 902 associated with the threshold amplitude change. A phase change 906 between that phase measurement 902 and the subsequent phase measurement 902 is also shown. Because phase change 906 is not greater than phase threshold 904, system 600 may determine that a scalar translocation of the electrode lead has not occurred, but, rather, that the threshold amplitude change of amplitude drop 806 is caused by something other than a scalar translocation of the electrode lead (e.g., such as by the electrode configuration measuring the evoked responses passing the stimulation frequency depth).

In sum, system 600 may determine whether the scalar translocation of the electrode lead has occurred by, first, determining that an amplitude change (e.g., one of amplitude drops 806) is greater than a predetermined amplitude threshold associated with a frequency at which the acoustic stimulation is applied (i.e., amplitude threshold 804). Subsequently, in response to the determination that the amplitude change is greater than the predetermined amplitude threshold, system 600 may determine that phase change 906 is less than phase threshold 904. Finally, in response to the determination that phase change 906 is less than phase threshold 904, system 600 may determine that a scalar translocation of the electrode lead has not occurred.

In another example, a graph 1000 shown in FIG. 10 illustrates a plurality of phase measurements 1002 plotted along graph 1000 with respect to time, similar to graph 900. As shown, a predetermined phase threshold 1004-1 (e.g., a minimum threshold large enough to allow for minor phase changes but small enough to be surpassed by a phase change of approximately 180°) is depicted relative to a first phase measurement 1002 associated with the threshold amplitude change. Additionally, another predetermined phase threshold 1004-2 (e.g., a maximum threshold large enough to not be surpassed by a phase change of approximately 180° but small enough to be surpassed by a phase change of approximately 360°) is also shown. A phase change 1006 between the first phase measurement 1002 associated with the threshold amplitude change and the subsequent phase measurement 1002 is also illustrated. Because phase change 1006 is greater than phase threshold 1004-1, system 600 may, in certain examples, determine that a scalar translocation of the electrode lead has occurred. However, because phase change 1006 is also greater than phase threshold 1004-2, system 600 may instead, in other examples, determine that the threshold amplitude change of amplitude drop 806 is caused by something other than a scalar translocation of the electrode lead (e.g., such as by the electrode configuration measuring the evoked responses passing the stimulation frequency depth). This is because phase change 1006 is so large (approximately 360°) that it actually may represent a relatively minor phase change that only appears large due to an artifact of how evoked responses are measured and/or represented. In reality, a phase change of 360° may be identical to a phase change of 0°; thus, certain implementations may set both a minimum and a maximum phase threshold 1004 (i.e., minimum phase threshold 1004-1 and maximum phase threshold 1004-2) to ensure that phase change 1006 is within range of the 180° phase change that is expected to be measured if a scalar translocation of the electrode lead has occurred.

In yet another example, a graph 1100 shown in FIG. 11 illustrates a plurality of phase measurements 1102 plotted along graph 1100 with respect to time, similar to graphs 900 and 1000. As in graphs 900 and 1000, a predetermined phase threshold 1104 (e.g., a threshold large enough to allow for minor phase changes but small enough to be surpassed by a phase change of approximately 180°) is depicted relative to a first phase measurement 1102 associated with the threshold amplitude change. In this example, phase threshold 1104 may represent a minimum phase threshold (i.e., analogous to phase threshold 1004-1). However, it will be understood that a maximum phase threshold analogous to phase threshold 1004-2 may additionally or alternatively be included in other similar examples. A phase change 1106 between the first phase measurement 1102 associated with the threshold amplitude change and the subsequent phase measurement 1102 is also shown. Because phase change 1106 is greater than phase threshold 1104, system 600 may determine that a scalar translocation of the electrode lead has occurred.

In sum, system 600 may determine whether the scalar translocation of the electrode lead has occurred by, first, determining that an amplitude change (e.g., one of amplitude drops 806) is greater than a predetermined amplitude threshold associated with a frequency at which the acoustic stimulation is applied (i.e., amplitude threshold 804). Subsequently, in response to the determination that the amplitude change is greater than the predetermined amplitude threshold, system 600 may determine that phase change 1106 is greater than phase threshold 1104. Finally, in response to the determination that phase change 1106 is greater than phase threshold 1104, system 600 may determine that the scalar translocation of the electrode lead has occurred.

Figure 12:
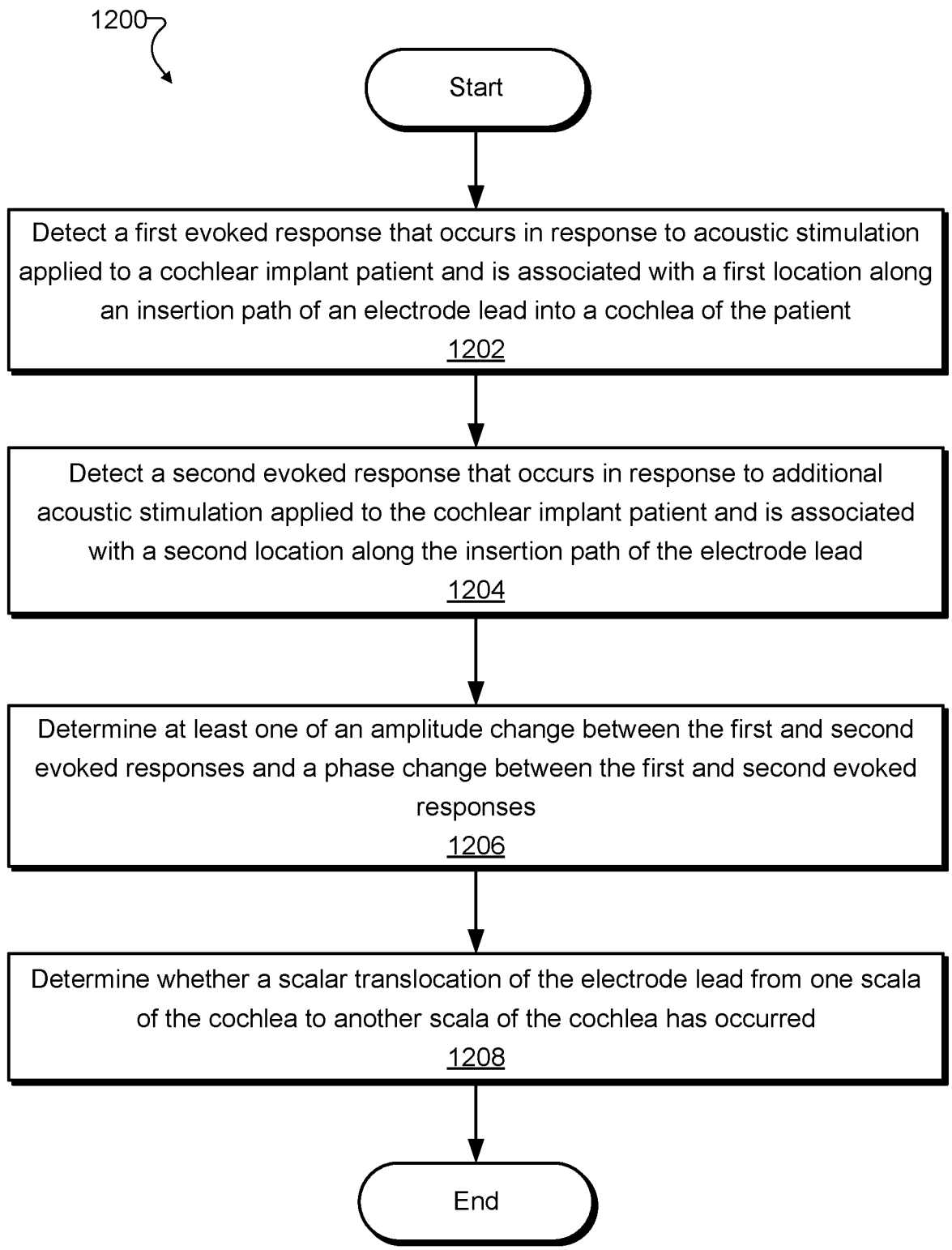
FIG. 12 illustrates an exemplary method for detecting scalar translocation of an electrode lead within a cochlea of a cochlear implant patient according to principles described herein.

FIG. 12 illustrates a method 1200 for detecting scalar translocation of an electrode lead within a cochlea of a cochlear implant patient. One or more of the operations shown in FIG. 12 may be performed by system 600 and/or any implementation thereof. While FIG. 12 illustrates exemplary operations according to one embodiment, other embodiments may omit, add to, reorder, and/or modify any of the operations shown in FIG. 12.

In operation 1202, a scalar translocation detection system associated with (e.g., communicatively coupled with, integrated by, etc.) a cochlear implant system may detect a first evoked response that occurs in response to acoustic stimulation applied to a cochlear implant patient. For example, the scalar translocation detection system may detect the first evoked response by way of an electrode configuration including at least one electrode disposed on an electrode lead included within the cochlear implant system and while the electrode configuration is positioned at a first location along an insertion path of the electrode lead into a cochlea of a cochlear implant patient. Operation 1202 may be performed in any of the ways described herein.

In operation 1204, the scalar translocation detection system may detect a second evoked response that occurs in response to additional acoustic stimulation applied to the cochlear implant patient. For instance, the scalar translocation detection system may detect the second evoked response by way of the electrode configuration while the electrode configuration is positioned at a second location along the insertion path of the electrode lead into the cochlea. Operation 1204 may be performed in any of the ways described herein.

In operation 1206, the scalar translocation detection system may determine at least one of an amplitude change and a phase change between the first and second evoked responses detected in operations 1202 and 1204, respectively. Operation 1206 may be performed in any of the ways described herein.

In operation 1208, the scalar translocation detection system may determine whether a scalar translocation of the electrode lead from one scala of the cochlea to another scala of the cochlea has occurred. In some examples, the scalar translocation detection system may determine whether the scalar translocation of the electrode lead has occurred based on the at least one of the amplitude change and the phase change determined in operation 1206. Operation 1208 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium (e.g., a memory, etc.) and executes the instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), erasable programmable read-only memory ("EPROM"), electrically erasable programmable read-only memory ("EEPROM"), a Flash EEPROM device, any other memory chip or cartridge, or any other tangible medium from which a computer can read.

Figure 13:
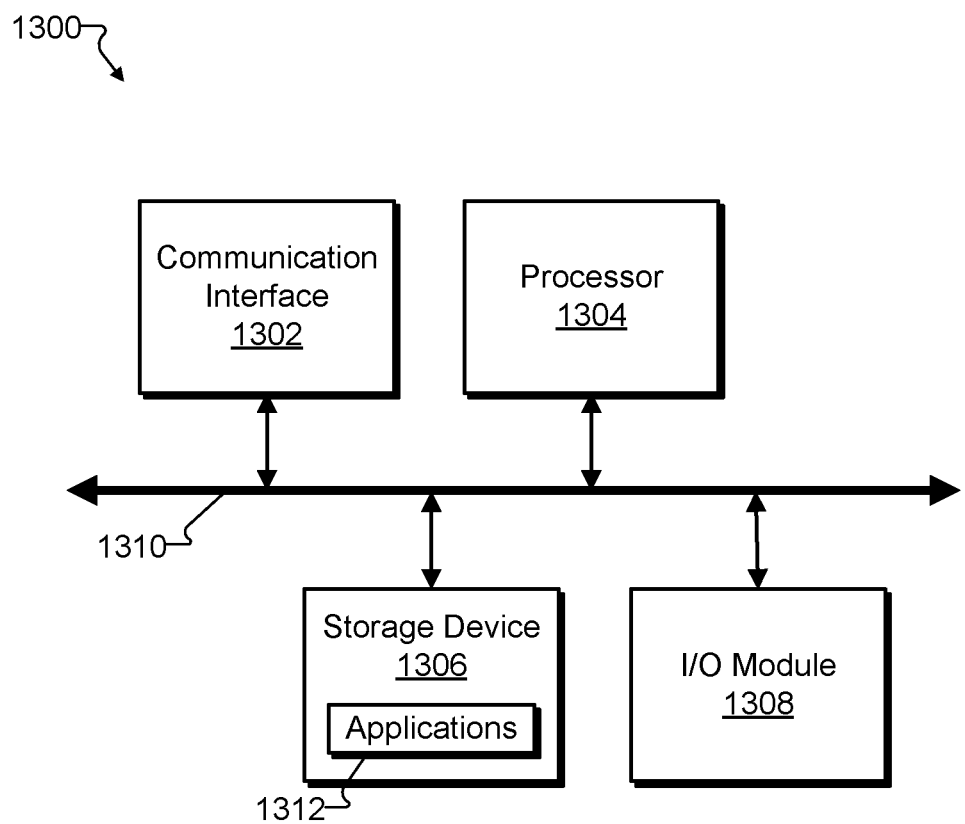
FIG. 13 illustrates an exemplary computing device according to principles described herein.

FIG. 13 illustrates an exemplary computing device 1300 that may be specifically configured to perform one or more of the processes described herein. As shown in FIG. 13, computing device 1300 may include a communication interface 1302, a processor 1304, a storage device 1306, and an input/output ("I/O") module 1308 communicatively connected via a communication infrastructure 1310. While an exemplary computing device 1300 is shown in FIG. 13, the components illustrated in FIG. 13 are not intended to be limiting. Additional or alternative components may be used in other embodiments. Components of computing device 1300 shown in FIG. 13 will now be described in additional detail.

Communication interface 1302 may be configured to communicate with one or more computing devices. Examples of communication interface 1302 include, without limitation, a wired network interface (such as a network interface card), a wireless network interface (such as a wireless network interface card), a modem, an audio/video connection, and any other suitable interface.

Processor 1304 generally represents any type or form of processing unit capable of processing data or interpreting, executing, and/or directing execution of one or more of the instructions, processes, and/or operations described herein. Processor 1304 may direct execution of operations in accordance with one or more applications 1312 or other computer-executable instructions such as may be stored in storage device 1306 or another computer-readable medium.

Storage device 1306 may include one or more data storage media, devices, or configurations and may employ any type, form, and combination of data storage media and/or device. For example, storage device 1306 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1306. For example, data representative of one or more executable applications 1312 configured to direct processor 1304 to perform any of the operations described herein may be stored within storage device 1306. In some examples, data may be arranged in one or more databases residing within storage device 1306.

I/O module 1308 may be configured to receive user input and provide user output and may include any hardware, firmware, software, or combination thereof supportive of input and output capabilities. For example, I/O module 1308 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1308 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1308 is configured to provide graphical data to a display for presentation to a user. The graphical data may be representative of one or more graphical user interfaces and/or any other graphical content as may serve a particular implementation.

In some examples, any of the facilities or systems described herein may be implemented by or within one or more components of computing device 1300. For example, one or more applications 1312 residing within storage device 1306 may be configured to direct processor 1304 to perform one or more processes or functions associated with evoked response detection facility 602 or processing facility 604 within system 600. Likewise, storage facility 606 within system 600 may be implemented by or within storage device 1306.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
   directing a loudspeaker to apply acoustic stimulation to a cochlear implant patient while an electrode lead is inserted into a cochlea of the cochlear implant patient;
   detecting, by way of a first electrode on the electrode lead while the first electrode is positioned at a first location in the cochlea, a first evoked response to the acoustic stimulation;
   detecting, by way of a second electrode on the electrode lead while the second electrode is positioned at a second location in the cochlea, a second evoked response to the acoustic stimulation;
   determining, based on an amplitude change between the first and second evoked responses, that a scalar translocation of the electrode lead from one scala of the cochlea to another scala of the cochlea has occurred; and
   based on the determination that the scalar translocation has occurred, notifying a user that the scalar translocation has occurred.

2. The method of claim 1, wherein the determination that the scalar translocation has occurred includes:
   determining the amplitude change between the first and second evoked responses;
   determining that the amplitude change is greater than a predetermined amplitude threshold associated with a frequency at which the acoustic stimulation is applied; and
   determining that the scalar translocation has occurred based on the determination that the amplitude change is greater than the predetermined amplitude threshold.

3. The method of claim 2, wherein:
   the determination that the scalar translocation has occurred further includes:
      determining a phase change between the first and second evoked responses, and
      determining that the phase change is greater than a predetermined phase threshold; and
   the determination that the scalar translocation has occurred is further based on the determination that the phase change is greater than the predetermined phase threshold.

4. The method of claim 1, wherein:
   the detecting of the first evoked response includes detecting a first cochlear microphonic electrocochleographic ("ECoG") potential occurring in response to the acoustic stimulation; and
   the detecting of the second evoked response includes detecting a second cochlear microphonic ECoG potential occurring in response to the acoustic stimulation.

5. The method of claim 1, wherein:
   the first electrode and the second electrode are both implemented by a same electrode that is nearest a distal end of the electrode lead; and
   the determination and the notifying of the user that the scalar translocation has occurred are performed in real time as the electrode lead is being inserted into the cochlea as part of an insertion procedure.

6. The method of claim 1, wherein:
   the first electrode is nearest a distal end of the electrode lead and the second electrode is a different electrode from the first electrode; and
   the determination and the notifying of the user that the scalar translocation has occurred are performed while the electrode lead remains stationary after an insertion procedure to insert the electrode lead into the cochlea is complete.

7. The method of claim 1, further comprising:
   tracking, based on the determination that the scalar translocation has occurred, trauma to the cochlea that is associated with the scalar translocation; and
   notifying the user, along with the notifying that the scalar translocation has occurred, regarding the trauma to the cochlea that is being tracked.

8. The method of claim 1, further comprising providing a user interface for use by the user, wherein the notifying that the scalar translocation has occurred is performed by way of the user interface.

9. The method of claim 1, wherein:
   the electrode lead is included within an electro-acoustic stimulation ("EAS") system that further includes the loudspeaker and a sound processor communicatively coupled to the loudspeaker; and
   the directing of the loudspeaker to apply the acoustic stimulation is performed using the sound processor.

10. A method comprising:
    directing a loudspeaker to apply acoustic stimulation to a cochlear implant patient while an electrode lead is inserted into a cochlea of the cochlear implant patient;
    detecting, by way of a first electrode on the electrode lead while the first electrode is positioned at a first location in the cochlea, a first evoked response to the acoustic stimulation;
    detecting, by way of a second electrode on the electrode lead while the second electrode is positioned at a second location in the cochlea, a second evoked response to the acoustic stimulation;
    determining, based on a phase change between the first and second evoked responses, that a scalar translocation of the electrode lead from one scala of the cochlea to another scala of the cochlea has occurred; and
    based on the determination that the scalar translocation has occurred, notifying a user that the scalar translocation has occurred.

11. The method of claim 10, wherein the determination that the scalar translocation has occurred includes:
    determining the phase change between the first and second evoked responses;

determining that the phase change is greater than a first predetermined phase threshold while also being less than a second predetermined phase threshold; and determining that the scalar translocation has occurred based on the determination that the phase change is greater than the first predetermined phase threshold and less than the second predetermined phase threshold.

12. The method of claim 11, wherein:

the determination that the scalar translocation has occurred further includes:
 determining an amplitude change between the first and second evoked responses, and
 determining that the amplitude change is greater than a predetermined amplitude threshold; and the determination that the scalar translocation has occurred is further based on the determination that the amplitude change is greater than the predetermined amplitude threshold.

13. The method of claim 10, wherein:

the detecting of the first evoked response includes detecting a first cochlear microphonic electrocochleographic ("ECOG") potential occurring in response to the acoustic stimulation; and the detecting of the second evoked response includes detecting a second cochlear microphonic ECoG potential occurring in response to the acoustic stimulation.

14. The method of claim 10, wherein:

the first electrode and the second electrode are both implemented by a same electrode that is nearest a distal end of the electrode lead; and the determination and the notifying of the user that the scalar translocation has occurred are performed in real time as the electrode lead is being inserted into the cochlea as part of an insertion procedure.

15. The method of claim 10, wherein:

the first electrode is nearest a distal end of the electrode lead and the second electrode is a different electrode from the first electrode; and the determination and the notifying of the user that the scalar translocation has occurred are performed while the electrode lead remains stationary after an insertion procedure to insert the electrode lead into the cochlea is complete.

16. The method of claim 10, further comprising:

tracking, based on the determination that the scalar translocation has occurred, trauma to the cochlea that is associated with the scalar translocation; and notifying the user, along with the notifying that the scalar translocation has occurred, regarding the trauma to the cochlea that is being tracked.

17. The method of claim 10, further comprising providing a user interface for use by the user, wherein the notifying that the scalar translocation has occurred is performed by way of the user interface.

18. The method of claim 10, wherein:

the electrode lead is included within an electro-acoustic stimulation ("EAS") system that further includes the loudspeaker and a sound processor communicatively coupled to the loudspeaker; and the directing of the loudspeaker to apply the acoustic stimulation is performed using the sound processor.

19. A system comprising:

a memory storing instructions; and one or more processors communicatively coupled to the memory and configured to execute the instructions to perform a process comprising:
 directing a loudspeaker to apply acoustic stimulation to a cochlear implant patient while an electrode lead is inserted into a cochlea of the cochlear implant patient;
 detecting, by way of a first electrode on the electrode lead while the first electrode is positioned at a first location in the cochlea, a first evoked response to the acoustic stimulation;
 detecting, by way of a second electrode on the electrode lead while the second electrode is positioned at a second location in the cochlea, a second evoked response to the acoustic stimulation;
 determining, based on at least one of an amplitude change or a phase change between the first and second evoked responses, that a scalar translocation of the electrode lead from one scala of the cochlea to another scala of the cochlea has occurred; and
 based on the determination that the scalar translocation has occurred, notifying a user that the scalar translocation has occurred.

20. The system of claim 19, wherein the determination that the scalar translocation has occurred includes:

determining both the amplitude change and the phase change between the first and second evoked responses;

determining that the amplitude change is greater than a predetermined amplitude threshold associated with a frequency at which the acoustic stimulation is applied;

determining that the phase change is greater than a predetermined phase threshold; and determining that the scalar translocation has occurred based on the determination that the amplitude change is greater than the predetermined amplitude threshold and the determination that the phase change is greater that the predetermined phase threshold.

* * * * *